(12) United States Patent  
Schulze

(10) Patent No.: US 8,187,274 B2  
(45) Date of Patent: May 29, 2012

(54) EXTERNAL FIXATOR

(75) Inventor: Dale R. Schulze, Fort Wayne, IN (US)

(73) Assignee: DePuy Products, Inc., Warsaw, IN (US)

( * ) Notice: Subject to any disclaimer, the term of this patent is extended or adjusted under 35 U.S.C. 154(b) by 862 days.

(21) Appl. No.: 12/165,251

(22) Filed: Jun. 30, 2008

(65) Prior Publication Data  
US 2009/0326532 A1 Dec. 31, 2009

(51) Int. Cl.  
A61F 5/04 (2006.01)

(52) U.S. Cl. ........................................................ 606/56

(58) Field of Classification Search .............. 606/54–59; 600/230, 234; 403/373, 316, 391  
See application file for complete search history.

(56) References Cited

U.S. PATENT DOCUMENTS

| | | | |
|---|---|---|---|
| 5,498,264 A | 3/1996 | Schlapfer et al. | |
| 5,752,954 A * | 5/1998 | Mata et al. | 606/59 |
| 6,080,153 A | 6/2000 | Mata et al. | |
| 6,565,564 B2 | 5/2003 | Hoffman et al. | |
| 6,616,664 B2 * | 9/2003 | Walulik et al. | 606/57 |
| 6,702,814 B2 | 3/2004 | Walulik et al. | |
| 7,041,103 B2 | 5/2006 | Hoffman-Clair et al. | |
| 7,048,735 B2 | 5/2006 | Ferrante et al. | |
| 7,320,556 B2 | 1/2008 | Vagn-Erik | |
| 7,491,008 B2 * | 2/2009 | Thomke et al. | 403/373 |
| 2002/0026190 A1 | 2/2002 | Walulik et al. | |
| 2002/0042613 A1 | 4/2002 | Mata | |
| 2006/0177263 A1 | 8/2006 | Thomke et al. | |
| 2006/0255521 A1 | 11/2006 | Brunner et al. | |
| 2006/0287652 A1 * | 12/2006 | Lessig et al. | 606/54 |
| 2007/0038217 A1 | 2/2007 | Brown et al. | |
| 2008/0065068 A1 * | 3/2008 | Thomke et al. | 606/57 |

FOREIGN PATENT DOCUMENTS

| | | |
|---|---|---|
| DE | 197 53 010 | 6/1999 |
| EP | 1862135 | 12/2007 |
| WO | WO 2007/024904 | 3/2007 |

OTHER PUBLICATIONS

Written Opinion of the International Searching Authority in corresponding PCT application (i.e., PCT/US2009/047612) mailed Oct. 8, 2009 (7 pages).  
Notification of Transmittal of the International Search Report and the Written Opinion of the International Searching Authority, or the Declaration (i.e., PCT/US2009/047612) mailed Oct. 8, 2009 (8 pages).  
Synthes website document "Large External Fixator—Tibial Shaft Box Frame", http://products.synthes.com/...; published at least as early as Jun. 29, 2008; (8 pages).

* cited by examiner

Primary Examiner — Pedro Philogene  
(74) Attorney, Agent, or Firm — Maginot, Moore & Beck

(57) ABSTRACT

An external fixator system includes a fixation bar, a fixation pin, and a clamp assembly. The clamp assembly includes a first jaw pair, a second jaw pair, and a first spring insert. The first jaw pair has a first upper jaw component and a first lower jaw component that collectively define a first passage configured to receive the fixation bar. The second jaw pair has a second upper jaw component and a second lower jaw component that collectively define a second passage configured to receive the fixation pin. The first spring insert is positioned within the first passage and interposed between the first upper jaw component and the first lower jaw component. Advancement of the fixation bar into the first passage causes deflection of the first spring insert.

15 Claims, 17 Drawing Sheets

EXTERNAL FIXATOR

FIELD

This application relates generally to the field of orthopaedics, and more specifically to external fixators used to secure reduced long bones.

BACKGROUND

External fixation is a surgical treatment used to set bone fractures in which a cast would not allow proper alignment of the fracture. In this kind of reduction, holes are drilled into uninjured areas of bones around the fracture and special bolts or wires are screwed or otherwise advanced into the holes. Outside the body, a rod or a curved piece of metal with special joints joins the bolts to make a rigid support. External fixation is usually used when internal fixation is contraindicated, often to treat open fractures, or as a temporary solution.

There are two main types of external fixation. One is known as mono-lateral fixation where the metal external structure is on one side of the limb. The other is circular fixation, in which the metal structure is circular or an arch and surrounds the limb. Installation of the external fixator is performed in an operating room, normally under general anesthesia. Removal of the external frame and bolts can be done with no anesthesia in an office visit. Circular fixation external fixators are often used for fractures of long bones that are weight bearing such as the femur and tibia. It is known that bearing weight through a fracture by walking on it, for example, with the added support of the external fixator frame actually helps fractures to heal.

Circular fixation external fixators typically include at least one ring. The ring surrounds the limb, for example the leg. Rods or distractors are connected to the ring and may engage a second, spaced apart, ring. Bone engaging pins are mounted onto the rings and/or the rods. The pins extend inwardly through soft tissue including skin and muscle and engage the bone near the fracture site. The pins may engage only the outer cortical bone or engage cancellous bone as well and may extend entirely through the bone. Adjustable clamps are used to connect the pins to the rods and to connect rods to each other at adjustable angular orietations.

Mono-lateral fixators typically include at least one bar onto which pins that similarly engage bone are secured by adjustable clamps similar those used in circular fixation external fixators. Bars may also be connected to each other by clamps. The clamps secure components such as the pins and the bars. The clamps include first jaws for grasping the bar and second jaws for grasping the pin or another bar. The components are aligned by partially tightening the clamps and lightly holding the jaws against the components while permitting the second jaw to move relative the first jaws and the components to slide within the jaws. The tightness of the jaws must be set very accurately to avoid having the components separate from the jaws of the clamps while positioning the components into the desired orientation. The components may also slip while tightening them into the final desired position. Since the pins must engage bone located below soft tissue, the proper positioning of the pins is difficult. The orienting of the components and rigid assembly of the fixator can be very challenging.

This time consuming difficult partial tightening of the fasteners and the exacting orientation of the components makes the surgery in which external fixators are installed slow and expensive and exposes the patient to risks associated with longer surgical procedures. Therefore, it would be advantageous to provide an improved external fixator.

SUMMARY

According to one embodiment of the present disclosure, there is provided an external fixator system. The system includes a fixation bar, a fixation pin, and a clamp assembly. The clamp assembly includes a first jaw pair, a second jaw pair, and a first spring insert. The first jaw pair has a first upper jaw component and a first lower jaw component that collectively define a first passage configured to receive the fixation bar. The second jaw pair has a second upper jaw component and a second lower jaw component that collectively define a second passage configured to receive the fixation pin. The first spring insert is positioned within the first passage and interposed between the first upper jaw component and the first lower jaw component. Advancement of the fixation bar into the first passage causes deflection of the first spring insert.

According to another embodiment of the present disclosure, there is provided a clamp assembly for use with fixation members. The clamp assembly includes a first jaw pair, a second jaw pair, and a first spring insert. The first jaw pair has a first upper jaw component and a first lower jaw component that collectively define a first passage configured to receive a first fixation member. The second jaw pair has a second upper jaw component and a second lower jaw component that collectively define a second passage configured to receive the second fixation member. The first spring insert is positioned within the first passage and interposed between the first upper jaw component and the first lower jaw component.

Other technical advantages of the present invention will be readily apparent to one skilled in the art from the following figures, descriptions and claims.

BRIEF DESCRIPTION OF THE DRAWINGS

For a more complete understanding of the present invention and the advantages thereof, reference is now made to the following description taken in connection with the accompanying drawings, in which.

Corresponding reference characters indicate corresponding parts throughout the several views. Like reference characters tend to indicate like parts throughout the several views.

DETAILED DESCRIPTION OF THE PREFERRED EMBODIMENTS

Embodiments of the present invention and the advantages thereof are best understood by referring to the following descriptions and drawings, wherein like numerals are used for like and corresponding parts of the drawings.

Figure 1:
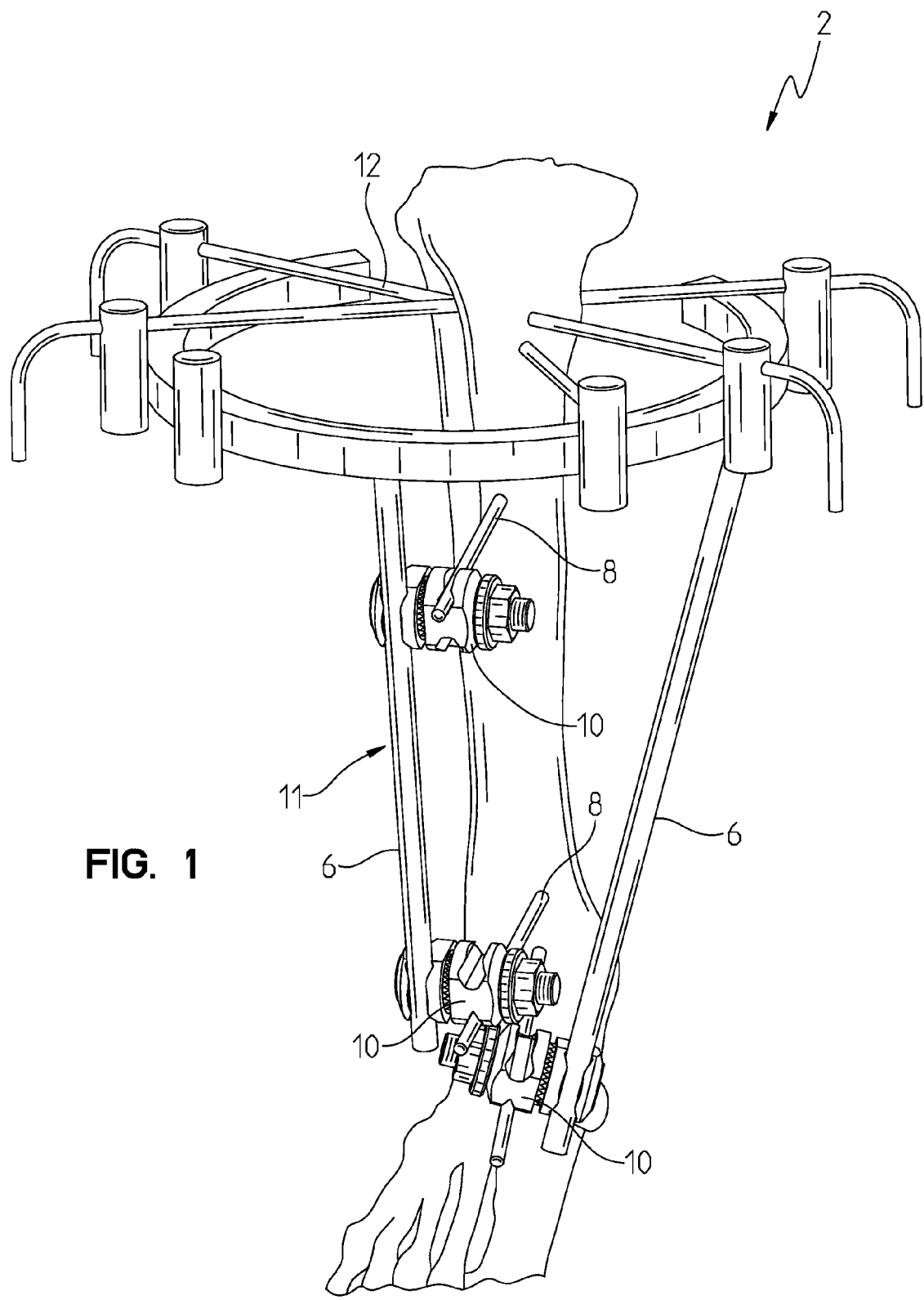
FIG. 1 depicts a perspective view of an external fixator system according to an embodiment of the present disclosure.

According to the present disclosure and referring now to FIG. 1, an external fixator system 2 is shown. The external fixator system 2 is used to support a long bone, for example, a femur, tibia, fibula, humerus, radius or ulna, or any other long bone of the human anatomy. The external fixator system 2 includes a fixation bar 6 and a fixation pin 8. The external fixator system 2 further includes a clamp assembly 10 for adjustably rigidly securing the pin 8 to the bar 6. It should be appreciated that the external fixator system 2 may include merely the fixation bar 6, the fixation pin 8 and the clamp assembly 10 to form a mono-lateral fixation device 11. Alternatively, the external fixator system 2 may be in the form of a circular fixation device and further include a ring 12 to which one or more fixation bars 6 may be secured.

It should be appreciated that, in addition to the first bar 6, additional bars 6 may be included in the external fixator system 2 and may extend from another bar 6 and/or from the ring 12. It should be appreciated that the clamp assemblies 10 may be used to rigidly, adjustably secure a pin to a bar, a pin to another pin or a bar to another bar.

Figure 2:
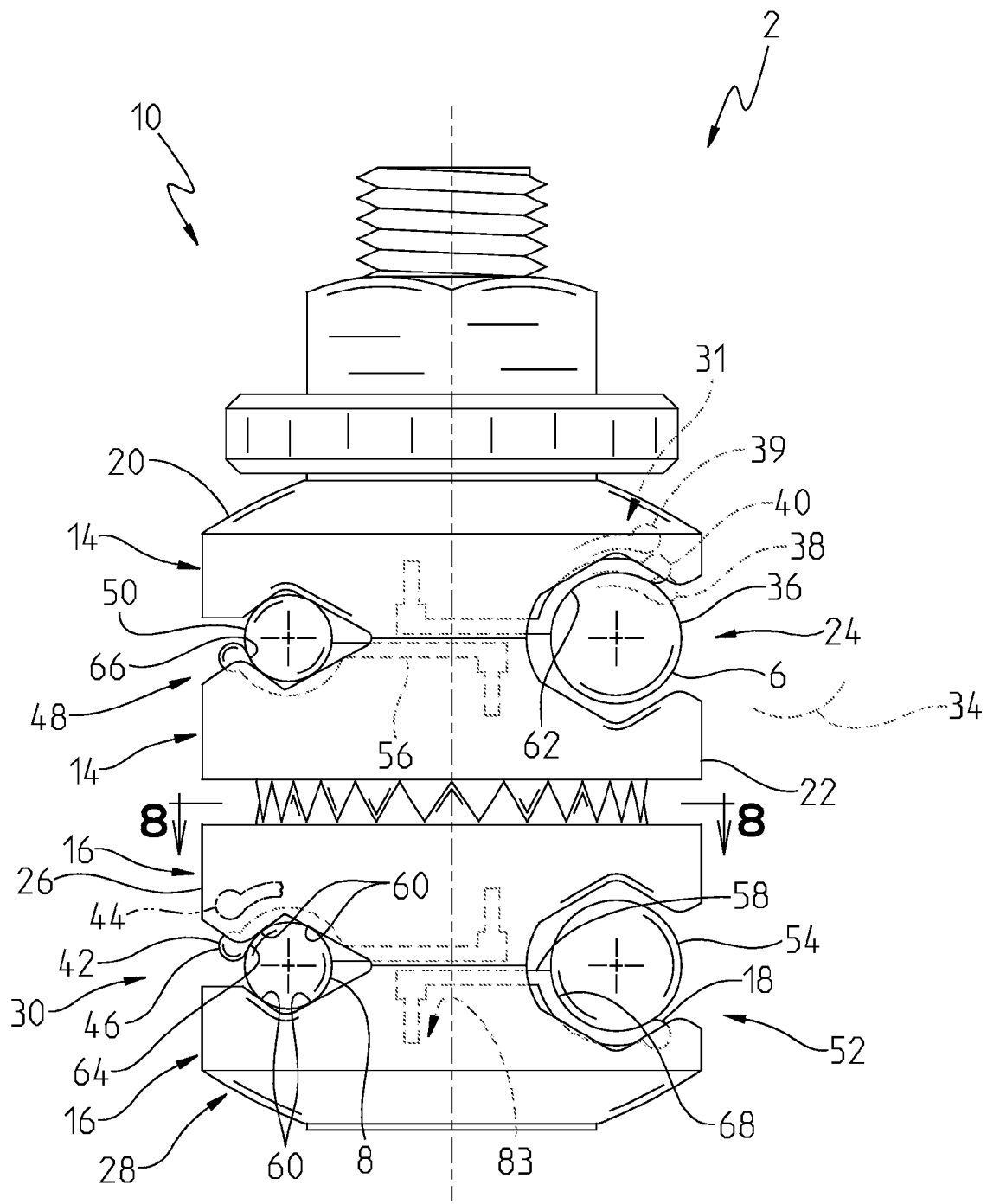
FIG. 2 depicts a plan view, partially in cross section of an embodiment of a clamp assembly for use in the external fixator system of FIG. 1 having cantilevered spring inserts, each with a solitary finger.

Referring now to FIG. 2, the clamp assembly 10 is shown in greater detail. The clamp assembly 10 includes a first jaw pair 14 and a second jaw pair 16. The clamp 10 also includes a first spring insert 18 that is utilized to secure the fixation bar 6 within the first jaw pair 14. The first jaw pair 14 includes a first upper jaw component 20 and a first lower jaw component 22. The jaw components 20 and 22 collectively define a first passage 24 configured to receive a fixation member in the form of, for example, fixation bar 6. The second jaw pair 16 includes a second upper jaw component 26 and a second lower jaw component 28. The jaw components 26 and 28 collectively define a second passage 30 configured to receive another fixation member in the form of, for example, fixation pin 8.

As shown in FIG. 2, the first spring insert 18 is positioned within the first passage 24 and interposed between the first upper jaw component 20 and the first lower jaw component 22. The first spring insert 18 urges the fixation bar 6 against the first lower jaw component 22 of the first jaw pair 14. The spring insert 18 keeps a lightly rigid configuration between the clamp assembly 10 and the fixation bar 6 such that the position of the bar 6 and the clamp assembly 10 may be temporarily securely positioned while adjusting the position of the fixation system on a patient. The first upper jaw component 20 includes a relief 31 for receiving the first spring insert 18 when deflected by the bar 6. The relief 31 permits the bar to be rigidly secured between the first upper jaw component 20 and the first lower jaw component 22 when the external fixator system is finally rigidly set and the clamps are finally rigidly tightened. The contact area of the first upper jaw component 20 is wider and more stable than the contact area of the first spring insert 18 and provides a more stable final rigid securement.

Continuing to refer to FIG. 2, as the fixation bar 6 is advanced in the direction of arrow 32, the bar 6 moves from first position 34, as shown in dash lines, to clamped position 36, as shown in phantom. As can be seen, advancement of the fixation bar 6 into the first passage 24 causes deflection of the first spring insert 18 from relaxed position 38, as shown in dashed lines, to second highly flexed position 39, as shown in phantom. Next, the first spring insert 18 moves fully into passage 24 to clamped position 40, as shown in solid, with the first spring insert 18 urging the fixation bar 6 against first lower jaw component 22.

While the clamp assembly 10 of the external fixator system 2 may include a first jaw pair 14 that is used to receive the fixation bar 6 and a second jaw pair 16 that is used to receive the fixation pin 8, it should be appreciated that the first jaw pair may receive any type of fixation member, and the second jaw pair may be used to receive any type of fixation member.

When the clamp assembly 10 is adjusted for use in the external fixator system 2, the first jaw pair 14 is permitted to rotate relative to the second jaw pair 16. The first upper jaw component 20 is spaced from the first lower jaw component 22, with the first spring insert 18 urging the bar 6 against the first lower jaw component 22. The first spring insert 18 is connected to first upper jaw component 20. Since the first spring insert 18 is so connected to first upper jaw component, the distance between the first upper jaw component 20 and the first lower jaw component 22 affects the clamping force of the first spring insert 18 against the bar 6. If, however, the first spring insert 18 were to be connected to the first lower jaw component 22, the clamping force of the first spring insert 18 against the bar 6 would be independent of the distance between the first upper jaw component 20 and the first lower jaw component 22. Such an alternate design may thus be advantageous.

While the fixation system 2 may include a clamping assembly 10 that is used to receive a solitary fixation bar and a solitary fixation pin, it should be appreciated that the clamping assembly 10 may be utilized to receive additional fixation members. For example, and as shown in FIG. 2, the clamp assembly 10 may further include a second spring insert 42 positioned within the second passage 30 and interposed between the second upper jaw component 26 and the second lower jaw component 28. The second spring insert 42 is similar to the first spring insert 18 and is utilized to urge the fixation pin 8 into contact with the second jaw pair 16. For example, and as shown in FIG. 2, advancement of the fixation pin 8 into the second passage 30 causes deflection of the second spring insert 42, similarly as the bar 6 deflects first spring insert 18, to deflect the second spring insert 42 into second spring insert position 44 as shown in phantom. After the pin 8 is in position in the passage 30, the second spring insert 42 is used to urge the pin 8 into contact with the second jaw pair 16, as with first spring insert 18 and bar 6. The second spring insert 42 is shown in operating position 46 in solid.

While the clamp assembly 10 of the external fixator system 2 may be utilized to secure a first fixation member in the form of a bar and a second fixation member in the form of, for example, a pin, it should be appreciated that the clamp assembly of the present disclosure may be utilized to secure additional fixation members. For example, and as shown in FIG. 2, The first upper jaw component 20 and the first lower jaw component 22 collectively define a third passage 48 configured to receive a first additional fixation member 50. Similarly, the second upper jaw component 26 and the second lower jaw component 28 collectively define a fourth passage 52 configured to receive a second additional fixation member 54. The first additional fixation member 50 and the second additional fixation member 52 may be any suitable fixation member and may, for example, be in the form of pins or bars. For example, as shown in FIG. 2, the first additional fixation member 50 is in the form of a second pin; and the second additional fixation member 54 is in the form of a second bar.

The clamp assembly 10 of the present disclosure may utilize the spring insert of the present disclosure only for cooperation with the bar 6, or for cooperation with the pin 8, or for cooperation with the bar 6 and the pin 8. It should be appreciated, however, that the clamp assembly 10 may utilize the spring inserts of the present disclosure on the second pin 50 and/or on the second bar 54. For example, and as shown in FIG. 2, the clamp assembly 10 may further include a third spring insert 56 positioned within the third passage 48 and interposed between the first upper jaw component 20 and the first lower jaw component 22. The advancement of the first additional fixation member 50 into the third passage 48 causes deflection of the third spring insert 56. The third spring insert 56 serves to urge the second pin 50 into a semi-rigid construct against the second jaw pair 16 such that the position of the second pin 50 is more rigidly positioned.

The clamp assembly 10 further includes a fourth spring insert 58 positioned within the fourth passage 52 and interposed between the second upper jaw component 26 and the second lower jaw component 28. The advancement of the second additional fixation member 54 into the second passage 52 causes deflection of the fourth spring insert 58. The fourth spring insert 58 serves to urge the second bar 54 into a rigid position with respect to the clamp assembly 10 so that the clamp assembly 10 may be accurately positioned prior to the final rigid assembly of the system 2.

The clamp assembly 10, including the upper jaw pair 14 having the first upper jaw component 20 and the first lower jaw component 22 and the second jaw pair 16 having the second upper jaw component 26 and the second lower jaw component 28, may have any suitable shape. As shown in FIG. 2, the jaw components 22, 20, 26 and 28 have a generally cylindrical shape and are generally solid, with some relief to maximize strength. Alternatively, the jaw components may be hollow, to minimize weight and cost. The jaw components 20, 22, 26 and 28 may include the passages 24, 30, 48 and 52 formed from the jaw components 20, 22, 26 and 28, with a shape for receiving the appropriate fixation member. The bar 6 and pin 8, as well as the second pin 48 and the second bar 54, have a generally cylindrical shape. Therefore, the passages 24, 30, 48 and 52 may, likewise, have a generally cylindrical shape and may be generally concave. Bars, pins, and their respective passages may, alternately, have other shapes besides being generally cylindrical. The passages 24, 30, 48 and 52 include contact points 60 for contact with the fixation members such that contact between the fixation members and the jaw pairs 16 and 18 may be reduced. The reduced contact results in an increase in the localized contact force which assists in rigid securement of the fixation members. The jaw components 22, 26 and 28 also have reliefs (not shown), similar to relief 31 in component 20.

The spring inserts 18, 42, 56 and 58 have a shape compatible with the fixation members. For example, and as shown in FIG. 2, the first spring insert 18 includes a first concave contact surface 62, the second spring insert 42 includes a second concave contact surface 64, the third spring insert 56 includes a third concave contact surface 66 and the fourth spring insert 58 includes a fourth concave contact surface 68. The contact surfaces 62, 64, 66 and 68 may have any concave shape and, as shown in FIG. 2, may have a shape that represents a segment of a circle. The first concave contact surface 62 is positioned in contact with the fixation bar 6 when the fixation bar 6 is located within the first passage 24, the second concave contact surface 64 is positioned in contact with the fixation pin 8 when the fixation pin 8 is located within the second passage 30, the third concave contact surface 66 is positioned in contact with the second pin 50 when the second pin 50 is located within the third passage 48, and the fourth concave contact surface 68 is positioned in contact with the second fixation bar 54 when the second bar 54 is located within the fourth passage 52.

Figure 3:
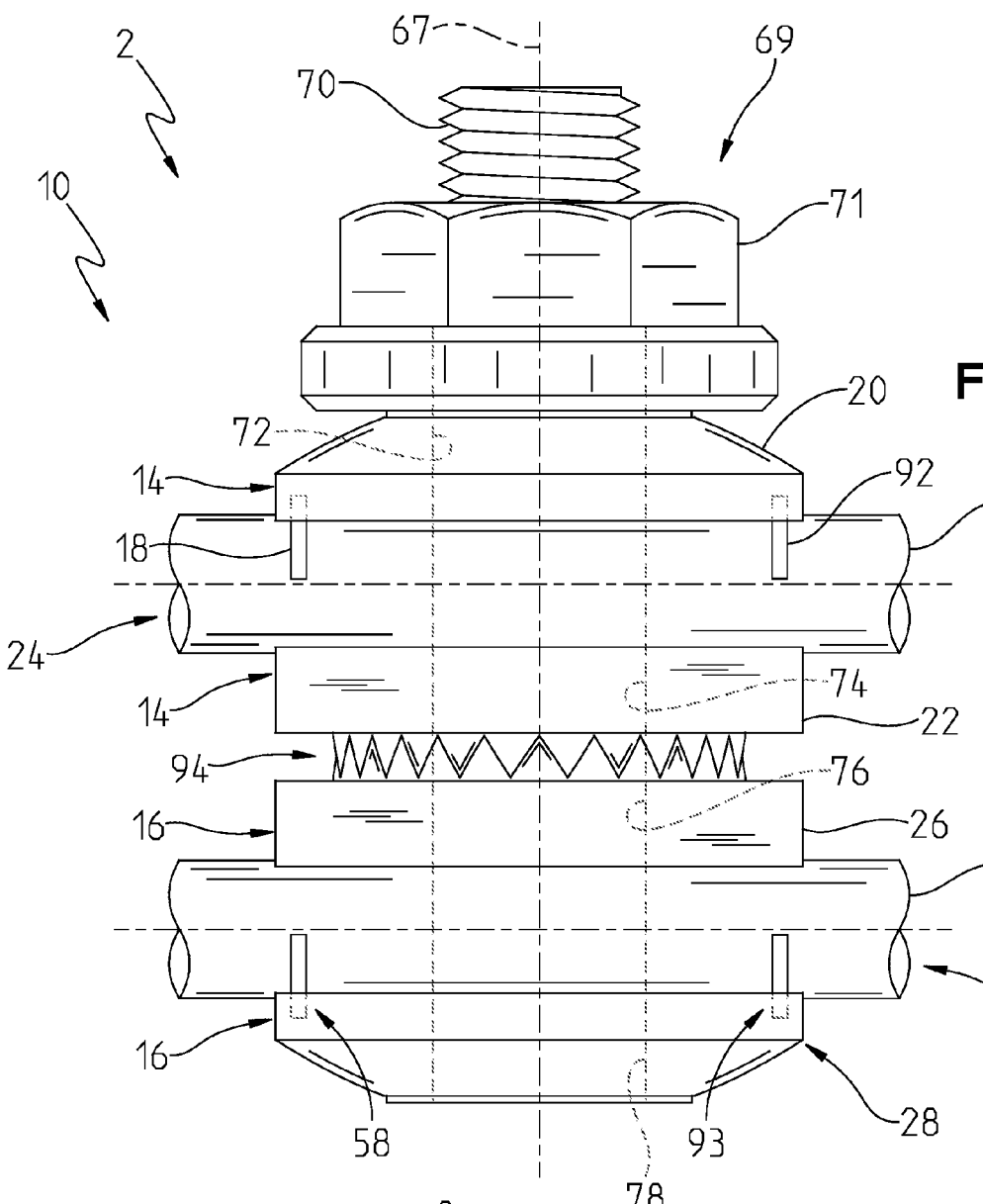
FIG. 3 depicts a side view of the clamp assembly of FIG. 2 showing the rod spring inserts engaging the rods.

Referring now to FIG. 3, the first jaw pair 14 and the second jaw pair 16 of clamp assembly 10 are shown in greater detail. The first jaw pair 14 may be secured to the second jaw pair 16 in any suitable fashion. For example, the first jaw pair 14 may be connected to the second jaw pair 16 by a fastener 69. The fastener 69 is centrally located along longitudinal axis 67 of the clamp assembly 10. Alternatively, the fastener may be eccentrically located. To permit the passage of the centrally located fastener 69 through the clamp assembly 10, the first upper jaw component 20 defines a first fastener passageway 72 extending through the first upper jaw component 20, the first lower jaw component 22 defines a second fastener passageway 74 extending through the first lower jaw component 22, the second upper jaw component 26 defines a third fastener passageway 76 extending through the second upper jaw component 26, and the second lower jaw component 28 defines a fourth fastener passageway 78 extending through the second lower jaw component 28.

The fastener 69 extends through each of the first fastener passageway 72, the second fastener passageway 74, the third fastener passageway 76, and the fourth fastener passageway 78. The fastener 69 is in the form of a cap screw 70 to which a nut 71 is threadably secured. When utilizing the fastener 69 to secure the clamp assembly 10, the fastener 69 is finger-tightened such that the first jaw pair 14 may rotate with respect to the second jaw pair 16 and such that the pin 8 may be properly aligned with the long bone 4. The first spring insert 18 and the second spring insert 42 serve to position the bar 6 and pin 8, respectively, while the fastener 69 is finger tightened such that the external fixator system 2 may be aligned with minimal difficulty.

Figure 4:
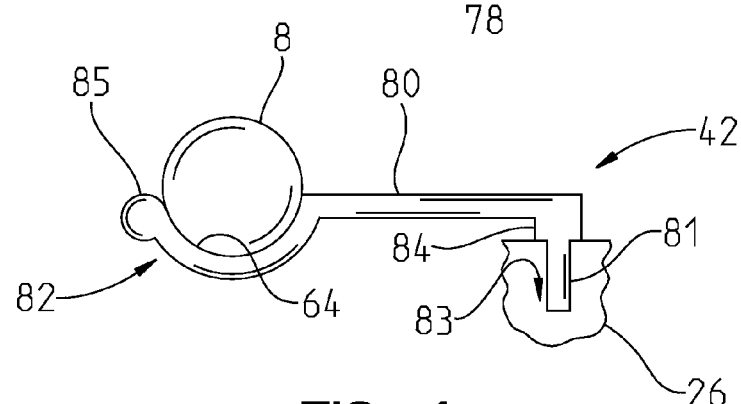
FIG. 4 depicts a plan view of a pin cantilevered spring insert for use in the clamp assembly of FIG. 1.

Referring now to FIG. 4, the second spring insert 42 for use with the fixation pin 8 to position the fixation pin 8 during adjustment of the external fixator system 2 is shown in greater detail. The second spring insert 42 is shown with a cantilevered design. The second spring insert 42 includes an arm 80. A pin 81 is secured to a first end of the arm 80 and an engaging end 82 is secured to the opposed end of the arm 80. The arm 80 may have any suitable shape and, as shown in FIG. 4, has a generally cylindrical shape in cross section. It should be appreciated that other shapes with varying cross-sectional dimensions and shapes may be used. The pin 81 may have any suitable shape and, for simplicity, may be cylindrical in cross section. The pin 81 fits into pocket 83 formed in the second upper jaw component 26 of the second jaw pair 16 of the clamp assembly 10. The pin 81 has a shoulder 84 for positioning the first spring insert 18 with respect to the second upper jaw component 26.

It should be appreciated that the second spring insert 42 may be alternatively secured to the second lower jaw component 28, instead of the second upper jaw component 26. The jaw component utilized for securing the spring insert may be selected to minimize the movement of the pin 8 as the fastener 69 is secured to the clamp assembly 10 and/or to maintain the spring force against the pin independently of the jaw component positions with respect to each other as described in greater detail earlier.

The second spring insert 42 further includes a nose 85 extending from the engaging end 82 of the bar 6. The engaging end 82 includes second concave contact surface 64 which engages the pin 8. The second concave contact surface 64 has a shape corresponding to the outer periphery of the pin 8 and is a sector of a cylinder. Alternatively, the second concave contact surface 64 may include recesses or raised portions for limited contact with the pin 8. The third spring insert 56, for simplicity, is identical to the second spring insert 42.

Figure 5:
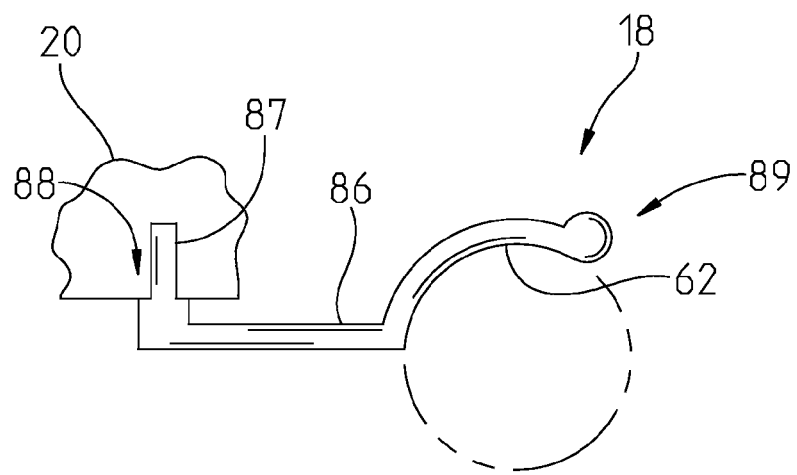
FIG. 5 depicts a plan view of a bar cantilevered spring insert for use in the clamp assembly of FIG. 1.

Referring now to FIG. 5, the first spring insert 18 is shown in greater detail. The first spring insert 18 is similar to the second spring insert 42 of FIG. 4, also having a cantilevered design. The first spring insert 18 includes an arm 86, similar to the arm 80 of the second spring insert 42. The first spring insert 18 includes a pin 87, extending from the arm 86. The pin 87 is fitted into pocket 88 formed in first upper jaw component 20 of the first jaw pair 14. It should be appreciated that, alternatively, the first spring insert 18 may be fitted into first lower jaw component 22. The pin 87 is similar to the pin 81 of the second spring insert 42. The first spring insert 18 further includes an engaging end 89, similar to engaging end 82 of the second spring insert 42.

Figure 6:
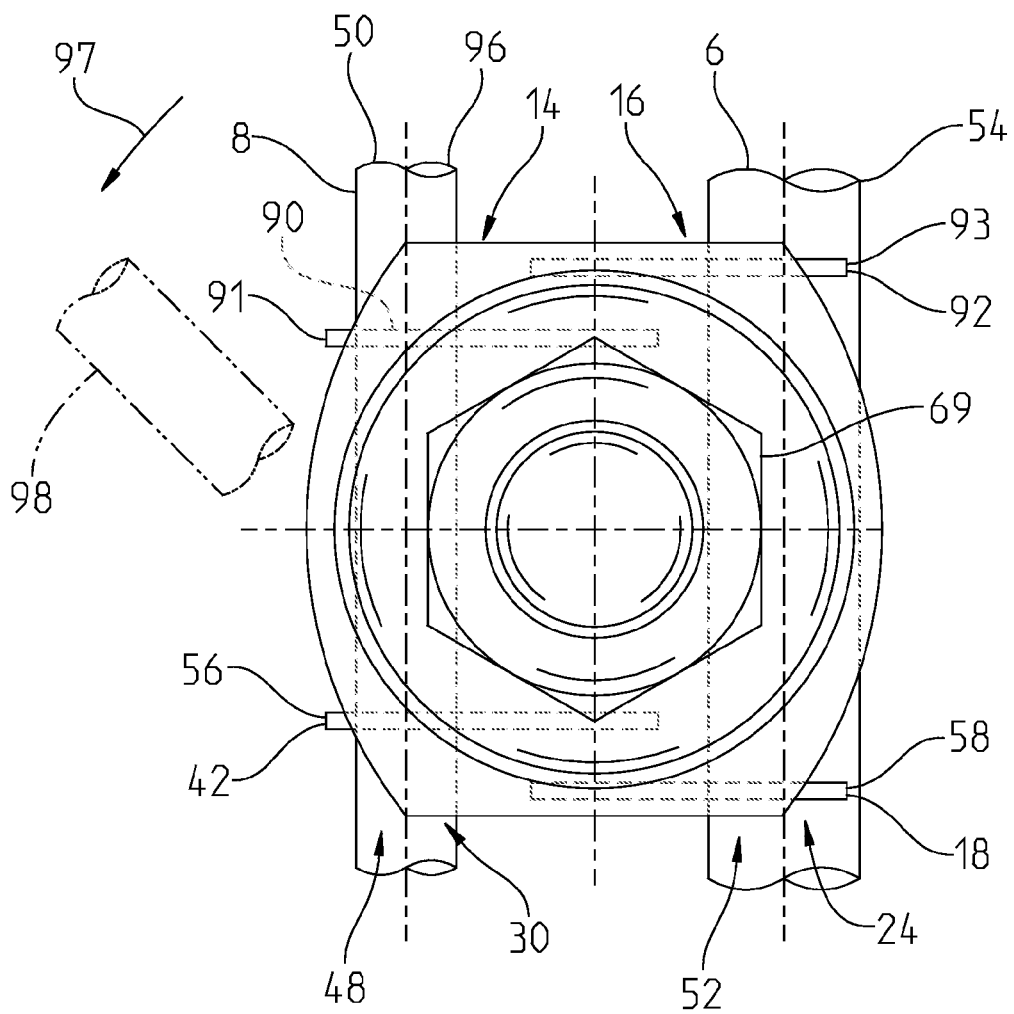
FIG. 6 depicts a top view of the clamp assembly of FIG. 2 showing the pin spring inserts engaging the pins and the bar spring inserts engaging the bars.

Referring now to FIG. 6, the first spring insert 18 and the second spring insert 42 are shown in a top view. The first spring insert 18 and the second spring insert 42 are spaced from the fastener 69. It should be appreciated that since the first spring insert 18 and the second spring insert 42 are spaced from the fastener 69, the first spring insert 18 is not centrally located with respect to the clamp assembly 10. Similarly, the second spring insert 42 is not centrally located with respect to the clamp assembly 10. As such, the spring inserts 18 and 42 may not be optimally positioned to secure the bar 6 and the pin 8, respectively, in the first passage 24 and the second passage 30, respectively, of the clamp assembly 10. Therefore, the clamp assembly 10 may include additional spring inserts positioned in the clamp assembly 10 to provide improved support for the bar 6 and the pin 8.

Figure 7:
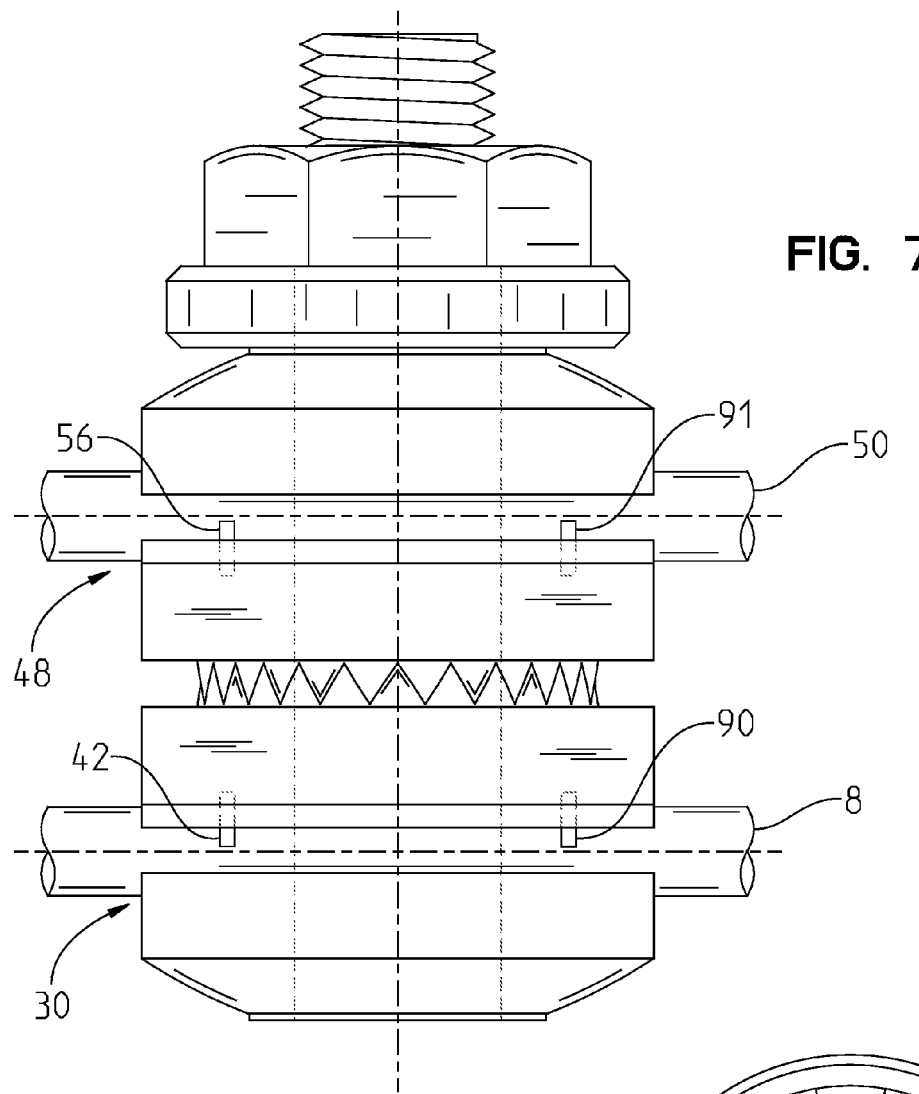
FIG. 7 depicts a side view of the clamp assembly of FIG. 2 showing the pin spring inserts engaging the rods.

For example and referring now to FIGS. 6 and 7, the clamp assembly 10 further includes a fifth spring insert 90 positioned in second passage 30 to assist the second spring insert 42 in securing the first fixation pin 8. Similarly, the clamp assembly 10 further includes a sixth spring insert 91 positioned in third passage 48 to assist the third spring insert 56 in securing the second fixation pin 50 in the third passage 48.

Referring now to FIGS. 3 and 6, the clamp assembly 10 further includes a seventh spring insert 92 positioned in first passage 24 for assisting the first spring insert 18 in securing first bar 6 within the first passage 24. Similarly, the clamp assembly 10 further includes an eighth spring insert 93 positioned in fourth passage 52 to assist the fourth spring 58 in securing the second bar 54 within the fourth passage 52.

Continuing to refer to FIG. 3, to properly align the fixation pin 8 with respect to the fixation bars 6 in the external fixator system 2, the clamp assembly 10 includes a connector 94 positioned between the first jaw pair 14 and the second jaw pair 16. The connector 94 permits the first jaw pair 14 to rotate around longitudinal center line 67 with respect to second jaw pair 16 to properly align the pin 8 with respect to the bar 6.

For example, and referring again to FIG. 6, the fixation pin 8 includes a first position 96 as shown in phantom. The second jaw pair 16 may be rotated with respect to first jaw pair 14 in the direction of arrow 97 such that the fixation pin 8 may move to second position 98 as shown in dashed lines.

Figure 8:
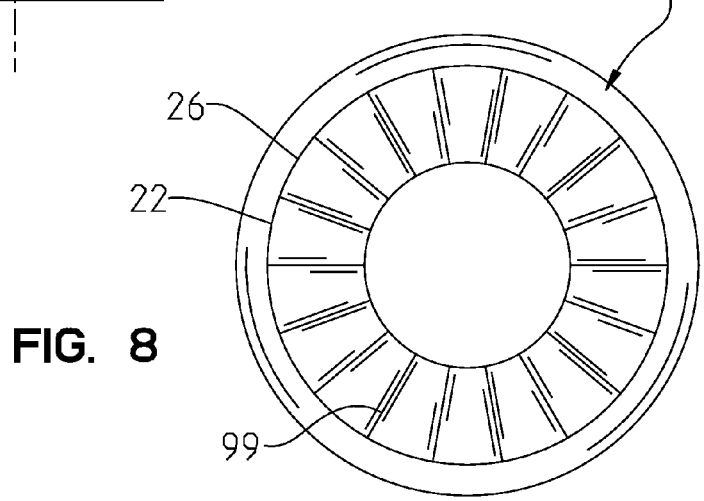
FIG. 8 depicts a cross sectional view of FIG. 2, along the lines 8-8 in the direction of the arrows, showing the radial splines used to connect the upper jaw pair to the lower jaw pair.

Referring now to FIG. 8, the connector 94 may have any suitable shape and may, for example, include matching radial splines 99 located on the first lower jaw component 22 and the second upper jaw component 26. The radial splines 99 provide for discrete angular rotation adjustments for the first jaw pair 14 with respect to the second jaw pair 16. For example, if the radial splines 99 have, for example, 36 splines, then each particular index of the first jaw pair 16 with respect to the second jaw pair 16 would represent ten degrees.

Referring now to FIGS. 9-12, another embodiment of the present disclosure is shown as clamp assembly 110. Clamp assembly 110 is for use in external fixator system 102. The external fixator system 102 is similar to the external fixator system 2 of FIG. 1. The clamp assembly 110 may replace clamp assembly 10 in the external fixator system 2 of FIG. 1. The clamp assembly 110 is similar to the clamp assembly 10 of FIGS. 2-8 except that the clamp assembly 110 includes spring inserts that have a different shape in comparison to the cantilevered spring inserts of the clamp assembly 10 of FIGS. 2-8. The clamp assembly 110 includes a first spring insert 118 having opposed first finger 151 and second finger 153. The fingers 151 and 153 secure the fixation members between the fingers 151 and 153.

Figure 9:
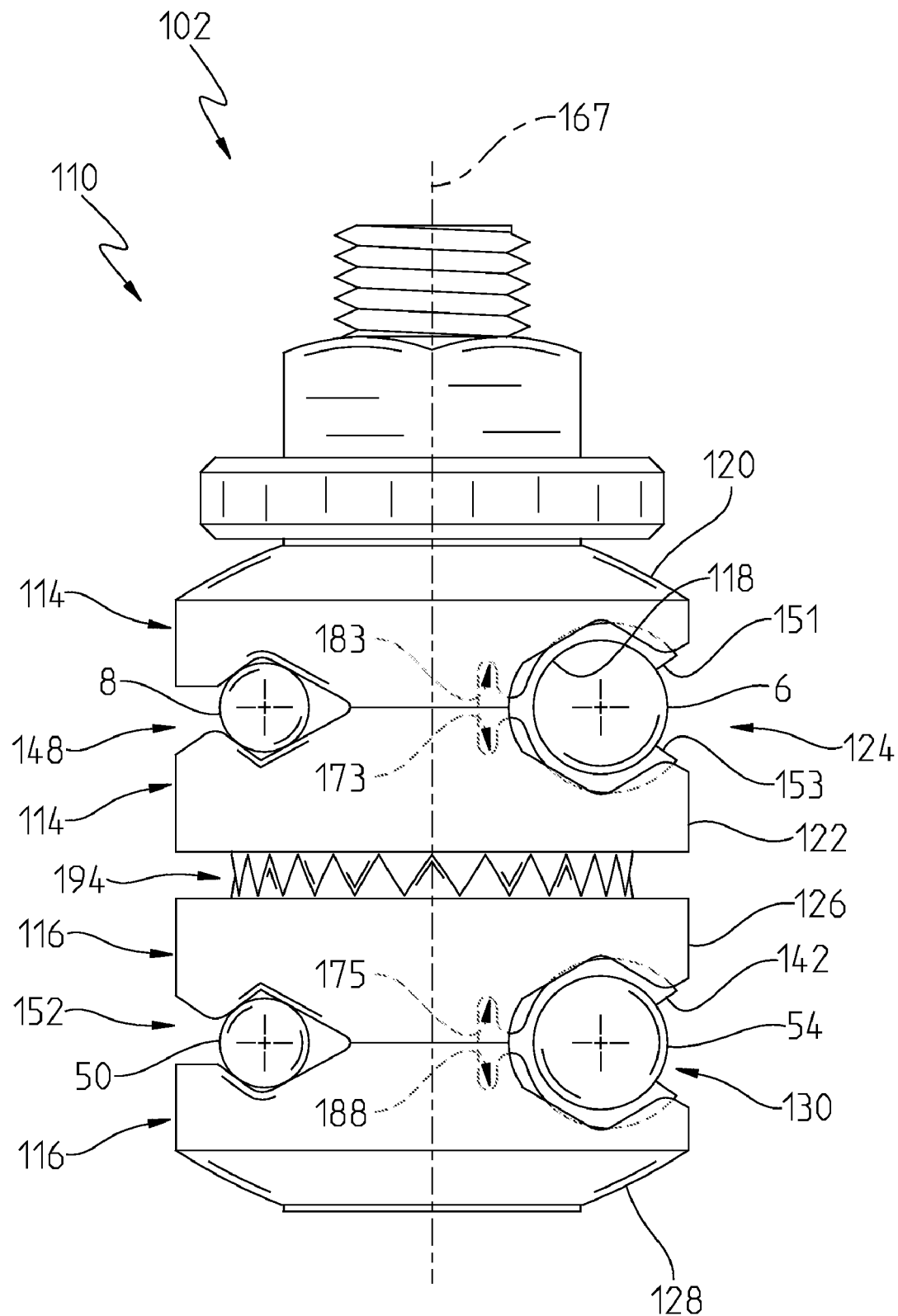
FIG. 9 depicts a plan view, partially in cross section, of another embodiment of a clamp assembly for use in the external fixator system of FIG. 1 having cantilevered spring inserts, each with two spaced apart fingers.

As shown in FIG. 9, the clamp assembly 110 includes a first jaw pair 114 and a second jaw pair 116 that is rotatably movable with respect to the first jaw pair along longitudinal axis 167 of the clamp assembly 110. A connector 194 secures the first jaw pair 114 to the second jaw pair 116. The first jaw pair 114 includes a first upper jaw component 120 and a first lower jaw component 122 that define a first passage 124 between the first upper jaw component 120 and the first lower jaw component 122 for receiving first fixation bar 6. The second jaw pair 116 includes a second upper jaw component 126 and a second lower jaw component 128 that defined a second passage 130 for receiving second fixation bar 54 between the components 126 and 128. A second spring insert 142 positions the second fixation bar 54 in the second passage 130. The second spring insert 142 may be identical to the first spring insert 118.

The first jaw pair 114, as shown, further includes a third passage 148 for securing a first fixation pin 8 between the first upper jaw component 120 and the first lower jaw component 122. Similarly, the second jaw pair 116 defines a fourth passage 152 between the second upper jaw component 126 and the second lower jaw component 128. The fourth passage 152 is configured to receive second fixation pin 50.

The clamp assembly 110 may be used to secure the pins 8 and 50 without the use of a spring insert. Alternatively, however, spring inserts (not shown) similar to the spring insert 118, but with a contact surface sized for the pins 8 and 50 may be used.

It should be appreciated that the clamp assembly of the present disclosure may have an arrangement to secure only two fixation members, one member on each jaw pair. In such an arrangement, each jaw pair may have only one passage. For example clamp assembly 110 may be utilized to clamp the first fixation bar 6 to the second fixation bar 54 and the first jaw pair 114 may include only first passage 124 for clamping the first fixation bar 6. Similarly, the second jaw pair 116 may include only second passage 130 for clamping the second fixation bar 54.

The first upper jaw component 120, the first lower jaw component 122, the second upper jaw component 126, and the second lower jaw component 128 may be similar to their respective jaw components 20, 22, 26 and 28 of the clamp assembly 10 of FIGS. 2-8. The jaw components 120, 122, 126 and 128 may include different features however, for securing the fixation members. For example, and as shown in FIG. 9, the first upper jaw component 120 includes a pocket 183 for receiving the first spring insert 118. Similarly, the first lower jaw component 122 includes a pocket 173 for receiving the first spring insert 118. Similarly, the second upper jaw component 126 includes a pocket 175 for receiving the second spring insert 142. Similarly, the second lower jaw component 128 includes a pocket 188 for receiving the second spring insert 142.

The first spring insert 118 is fitted into or extends into first passage 124 while the second spring insert 142 is fitted into second passage 52. The first spring insert 118 secures the first bar 6 during alignment of the external fixator system 102 while the second spring insert 142 secures the second bar 54 in the second passage 130 while the external fixator system 102 is aligned. The fingers 151 and 153 of the first spring insert 118 provide a clamping force for the first fixation bar 6 that is independent of the distance between the jaw components 120 and 122.

Figure 10:
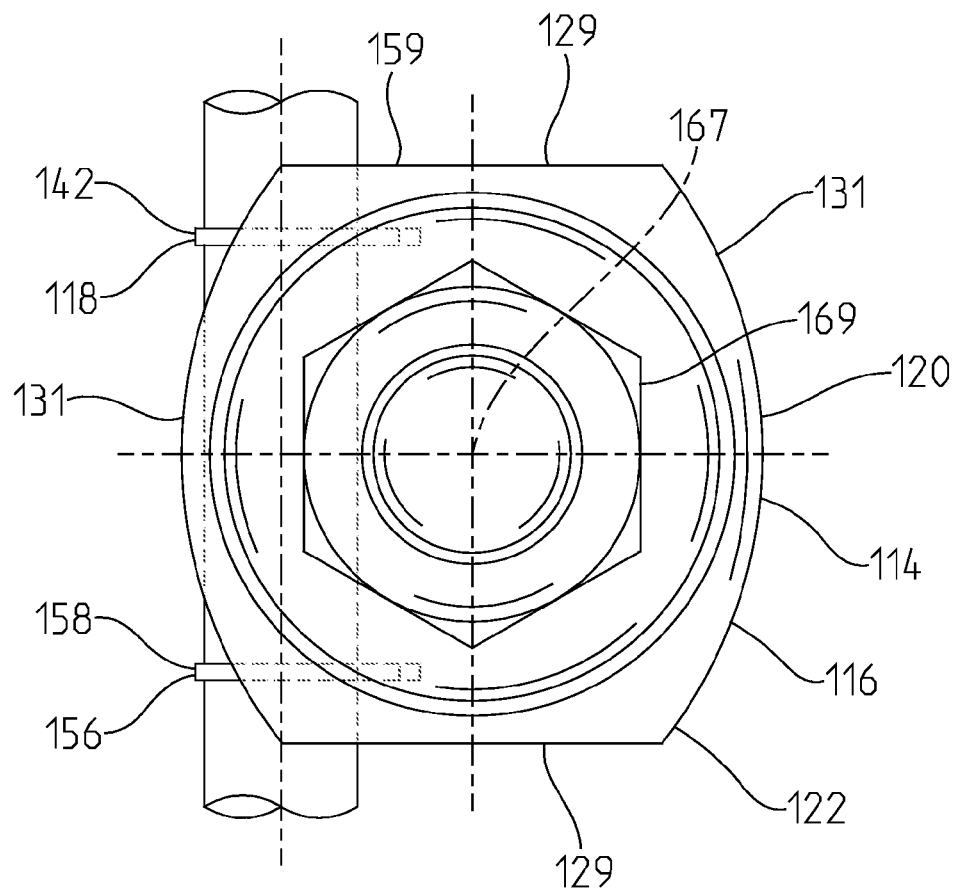
FIG. 10 depicts a top view of the clamp assembly of FIG. 9 showing the bar spring inserts engaging the bars.

Referring now to FIG. 10, the first spring insert 118 and the second spring insert 142 are spaced apart from fastener 169 which is utilized to secure the first jaw pair 114 to the second jaw pair 116. Since the first spring insert 118 and the second spring insert 142 are not centrally positioned with respect to longitudinal center line 167 of the clamp assembly 110, the first spring insert 118 and the second spring insert 142 do not optimally secure the fixation bar 6 and 42 in the clamp assembly 110. Therefore, the clamp assembly 110 further includes a third spring insert 156 opposed to the first spring insert 118 and a fourth spring insert 158 opposed to the second spring insert 142. The first jaw pair 14 and the second jaw pair 16 include a periphery 159 that has spaced apart planar portions 129 and spaced apart cylindrical portions 131. The spaced apart planar portions 129 serve to provide an alignment of the first jaw pair 114 to the second jaw pair 116 and to provide an alignment of the first upper jaw component 120 to the first lower jaw component 122 as well as to provide an alignment of the second upper jaw component 126 to the second lower jaw component 128.

Figure 11:
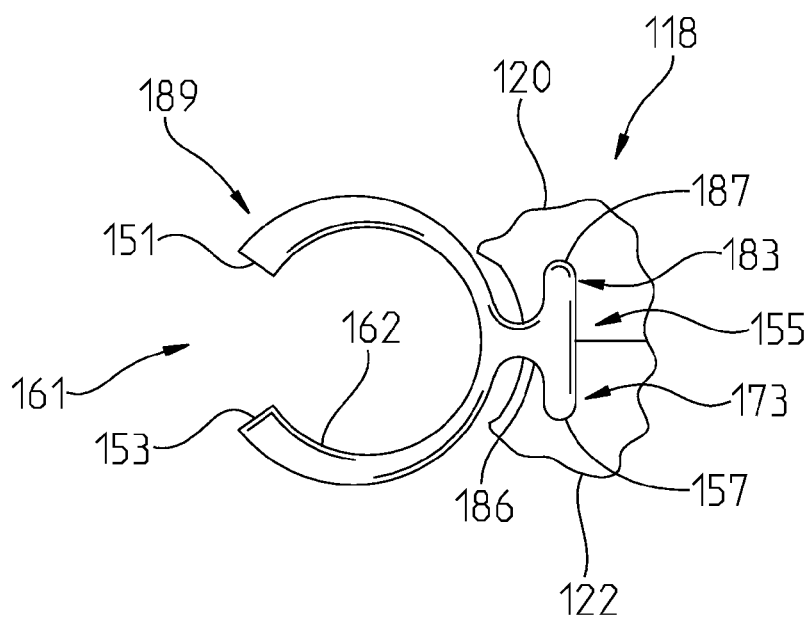
FIG. 11 depicts a plan view of a bar cantilevered spring insert with two spaced apart fingers for use in the clamp assembly of FIG. 9.

Referring now to FIG. 11, the first spring insert 118 is shown in greater detail. It should be appreciated that the second spring insert 142, the third spring insert 156, and the fourth spring insert 158 may all be similar or identical to the first spring insert 118. The spring insert 118 may be made of any suitable durable materials and may be made of materials similar to that of spring insert 18. For example, the spring insert 118 may be made of a polymer or steel.

The spring insert 118 includes an arm 186 from which a protrusion 155 extends. The protrusion 155 includes a first pin 187 for engagement with pocket 183 of the first upper jaw component 120. The protrusion 151 further includes a second pin 157 opposed to the first pin 187. The second pin 157 is sized for fitted engagement with pocket 173, formed in first lower jaw component 122. The first spring insert 118 further includes an engaging end 189 extending from the arm 186 and opposed to the protrusion 151. The engaging end 189 defines a concave surface 162 to which the bar 6 mattingly engages. The engaging end 189 includes the first finger 151 and the spaced-apart second finger 153. The fingers 151 and 153 define an opening 161 between the fingers 151 and 153. The opening 161 permits the bar 6 to be passed through the opening 161 to contact the concave surface 162 of the spring insert 118.

Figure 12:
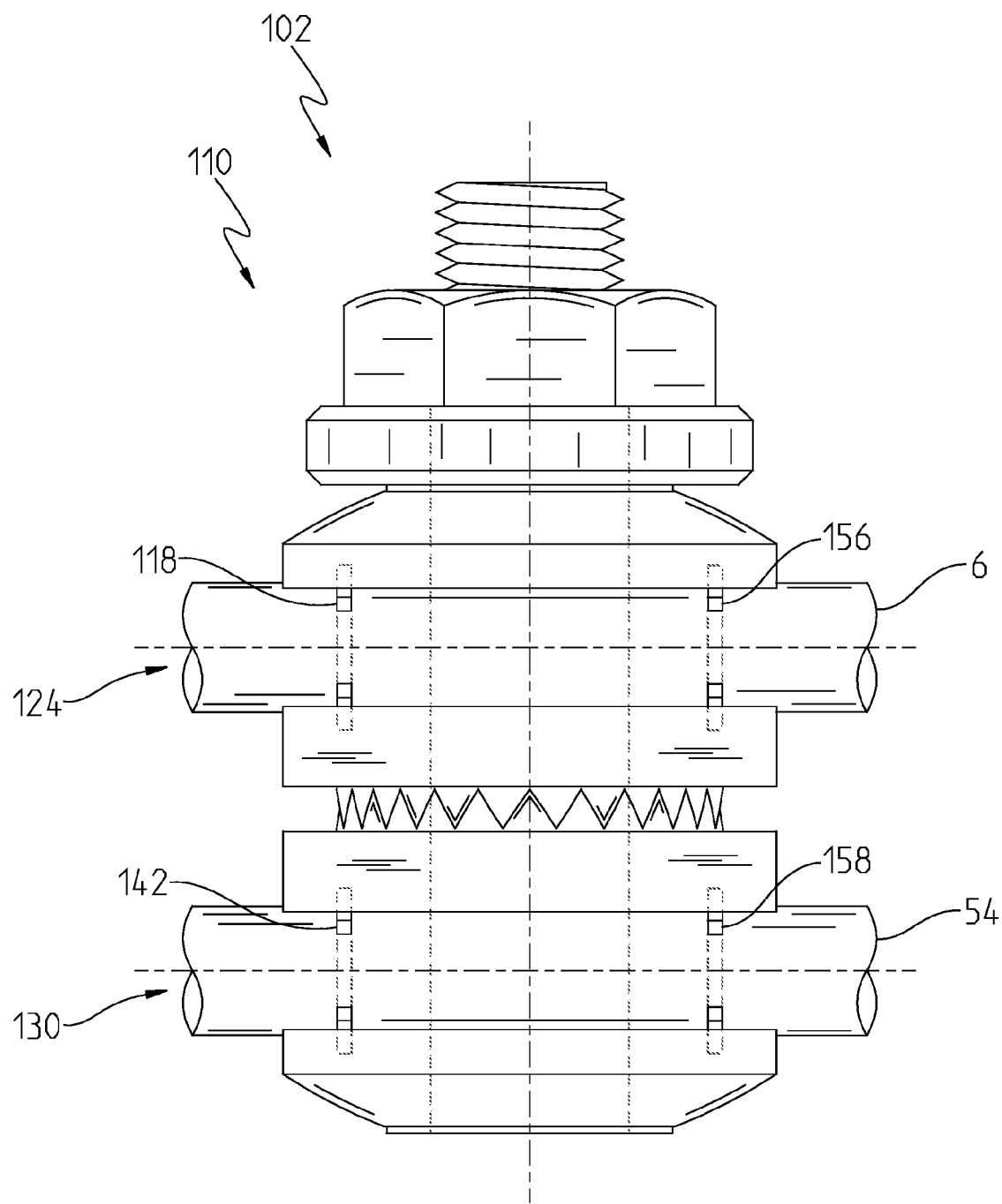
FIG. 12 depicts a side view of the clamp assembly of FIG. 9 showing the rod spring inserts engaging the rods.

Referring now to FIG. 12, the first fixation bar 6 and the second fixation bar 54 are shown in position within the first passage 124 and the second passage 130, respectively. The spring inserts 118 and 156 are used to positively position the first fixation bar 6 in the first passage 124 while the clamp assembly 110 is used to positively position the first fixation bar 6 and the second fixation bar 54 with respect to each other while the external fixator system 102 is positively positioned against the long bone of the patient. Similarly, the second spring insert 142 and the fourth spring insert 158 are used to positively position the second fixator bar 54 in the second passage 130 of the clamp assembly 110.

Referring now to FIGS. 13-17, another embodiment of the present invention is shown as clamp assembly 210. The clamp assembly 210 is similar to the clamp assembly 10 of FIGS. 2 through 8 except that the clamp assembly 210 includes spring inserts that are different in comparison to the spring inserts 18 of the clamp assembly 10 of FIGS. 2-8. The spring inserts of the clamp assembly 210 have opposed ends with each of the opposed ends fitting into a separate passage in the clamp assembly to reduce by 50 percent the number of spring inserts required for the clamp assembly 210 in comparison with the clamp assembly 10 of FIGS. 2-8. Further the spring insert of the clamp assembly 210 provides a force to the fixation member that is independent of the distance between adjacent jaw components.

Figure 13:
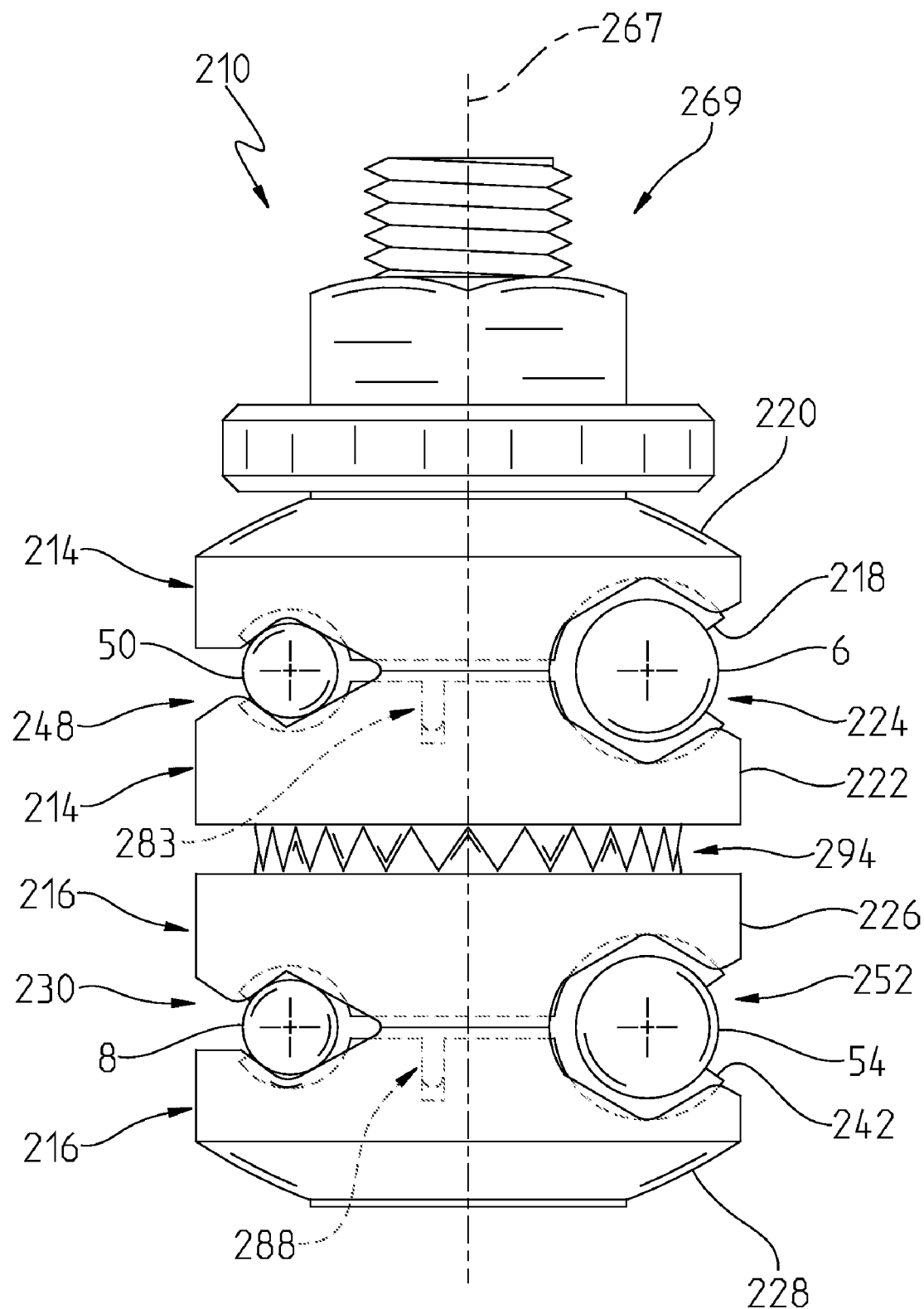
FIG. 13 depicts a plan view, partially in cross section, of another embodiment of a clamp assembly for use in the external fixator system of FIG. 1 having spring inserts with opposed clamping ends for engaging a pin and a bar.

As shown in FIG. 13, the clamp assembly 210 includes a first jaw pair 214, similar to the first jaw pair 14 of the clamp assembly 10 of FIGS. 2-8. The clamp assembly 210 further includes a second jaw pair 216, similar to the second jaw pair 16 of the clamp assembly 10 of FIGS. 2-8. The first jaw pair 214 is rotatably positionable with respect to the second jaw pair 216 about longitudinal center line 267 of the clamp assembly 210. The first jaw pair 214 is connected to the second jaw pair 216 by a connector 294, similar to the connector 94 of the clamp assembly 10 of FIGS. 2-8.

The first jaw pair 214 includes a first upper jaw component 220 and a first lower jaw component 222 which define a first passage 224 therebetween. The jaw components 220 and 222 are similar to the jaw components 222 and 20 of the clamp assembly 10 of FIGS. 2-8. The first lower jaw component 222 is different than the first upper lower component 22 of the clamp assembly 10 in that the first upper jaw component 222 includes a pocket 283 for receiving first spring insert 218.

The second jaw pair 216 includes a second upper jaw component 226 and a second lower jaw component 228 which define a fourth passage 252 between the jaw components 226 and 228. The jaw components 226 and 228 are similar to the jaw components 26 and 28 except that the second lower jaw component 228 includes a pocket 288 for receiving second spring insert 242

Figure 14:
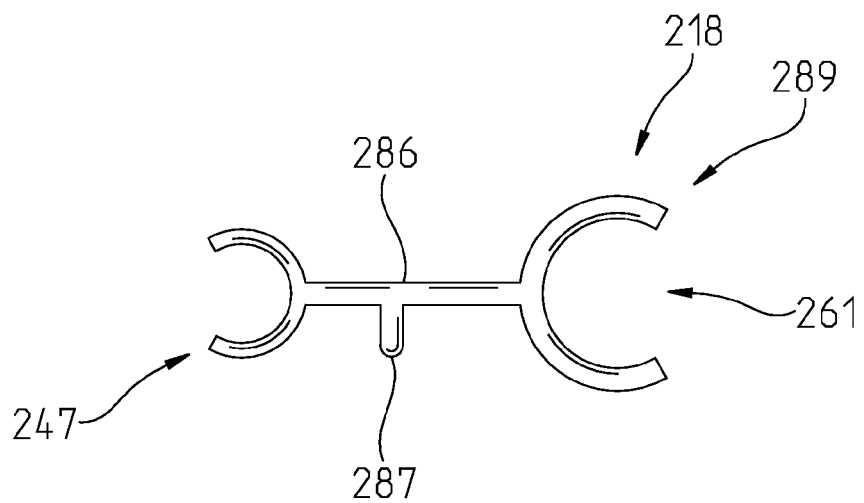
FIG. 14 depicts a plan view of a bar cantilevered spring insert with opposed clamping ends for use in the clamp assembly of FIG. 9.

Referring now to FIG. 14, the first spring insert 218 is shown in greater detail. The first spring insert 218 includes an arm 286 from which pin 287 extends. The pin 287 is mattingly fitted to pocket 283 formed in first lower jaw component 222. A first engaging end 289 of the first spring insert 218 extends from a first end of the arm 286, and a second engaging end 247 extends from the arm 286 in a direction opposed to the first engaging end 287. The first engaging end 289 cooperates with first fixation bar 6 to center the first fixation bar 6 within the first passage 224 of the clamp assembly 210. Similarly, the second engaging end 247 cooperates with the second fixation pin 50 to center the second fixation pin 50 within third passage 248 formed in the clamp assembly 10.

The first engaging end 289 includes a first finger 251 and a spaced-apart second finger 253. The first finger 251 and the second finger 253 define an opening 261 formed between the fingers 251 and 253. The fingers 251 and 253 further define a concave surface 262 with a shape that cooperates with the first fixation bar 6. The concave surface 262 may be a generally cylindrical surface to cooperate with a cylindrical fixation pin. It should be appreciated that if the fixation bar or pin has another shape, for example, that of a square hexagon or other geometric or non-geometric shape, the concave surface preferably conforms to the periphery of that fixation bar or pin.

The second engaging end 247 includes a first finger 263 and a spaced-apart second finger 265 defining an opening 249 between the first finger 263 and the second finger 265. The first finger 263 and the second finger 265 define a concave surface 264 for receiving the second fixation pin 50. It should be appreciated that the first spring insert 218 may have a shape such that it includes only solitary first fingers on the first engaging end and a solitary finger on the second engaging end. If a solitary finger is used with the spring insert, the finger may extend sufficiently around the fixation member to secure it in position. The second spring insert 242 may be identical to the second spring insert 218.

Figure 15:
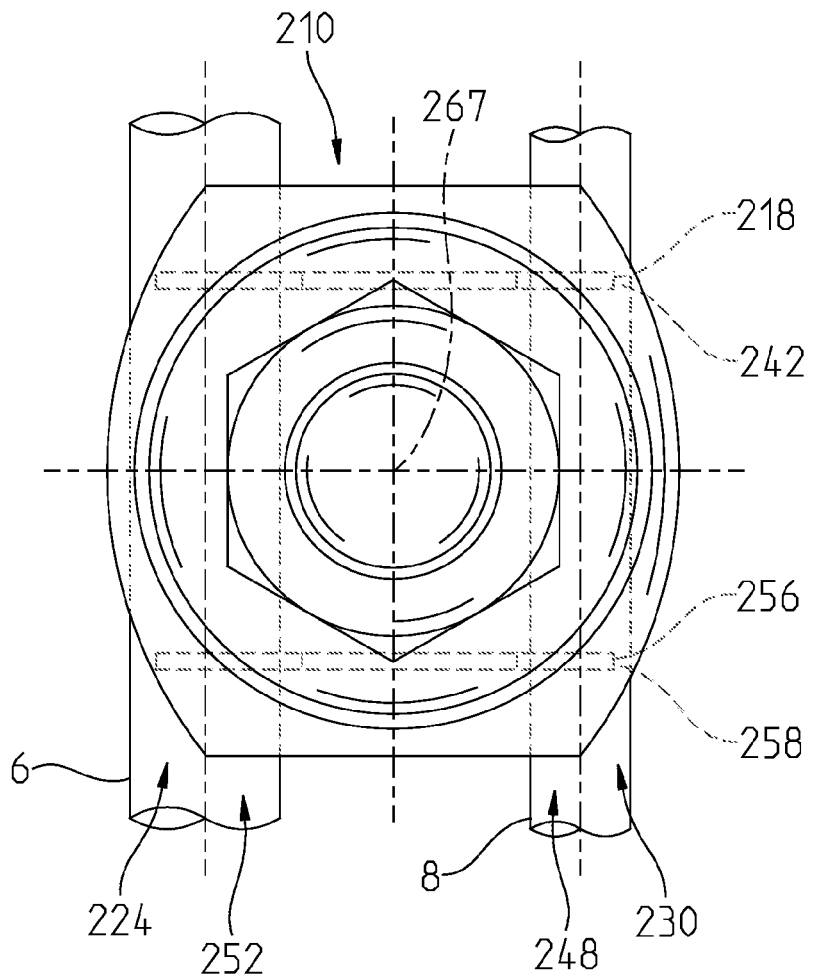
FIG. 15 depicts a top view of the clamp assembly of FIG. 13 showing the spring inserts engaging the pin and the bar.

Referring now to FIG. 15, the first spring insert 218 and the second spring insert 242 are spaced apart from fastener 269, which is utilized to secure the first jaw pair 218 to the second jaw pair 216. The spring inserts 218 and 242, when spaced from the fastener 269, are not positioned centrally with respect to longitudinal center line 267 of the clamp assembly 10, and, as such, may not optimally secure the first fixation bar 6 and the first fixation pin 8 within the clamp assembly 210.

Figure 16:
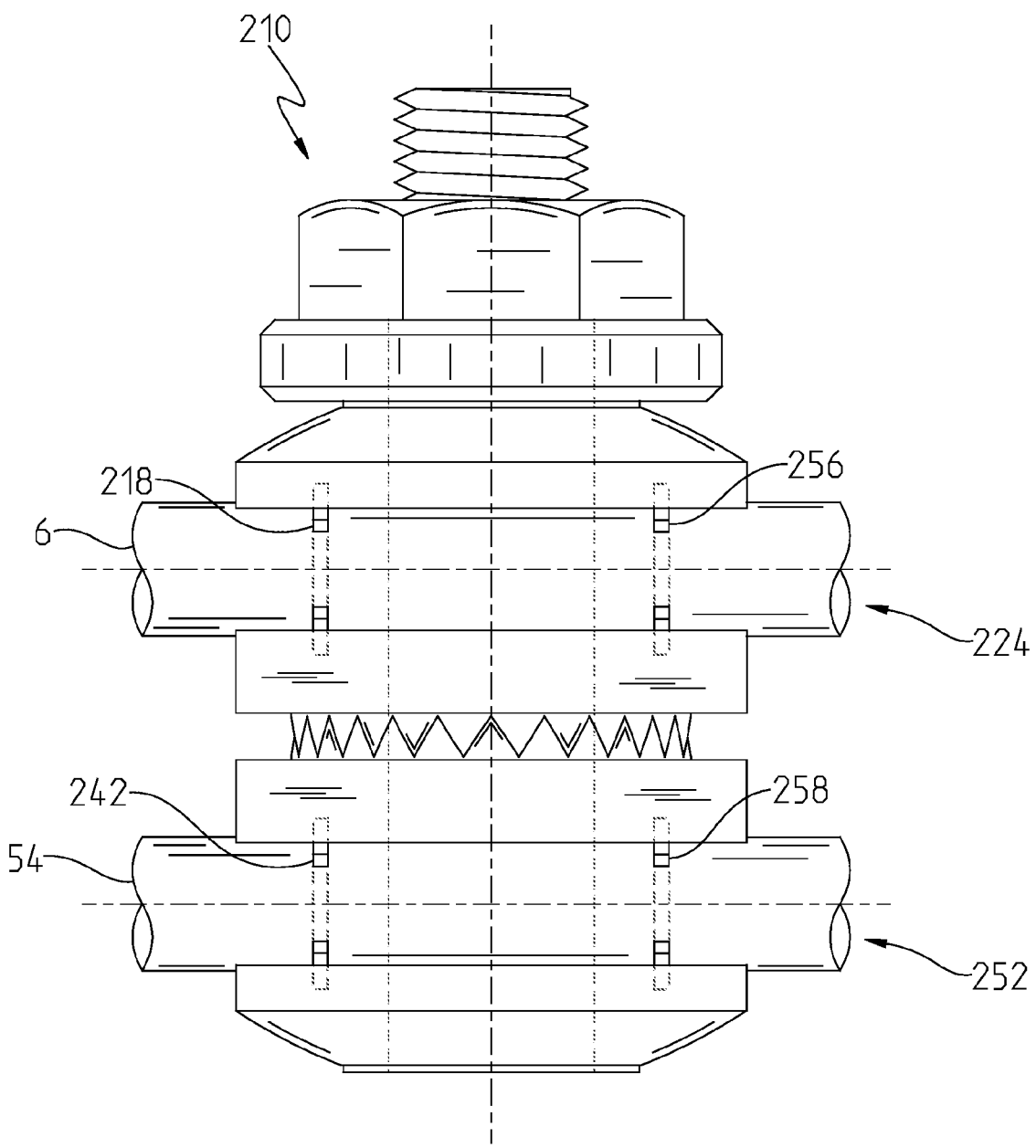
FIG. 16 depicts a side view of the clamp assembly of FIG. 13 showing the spring inserts engaging the rods.

Referring now to FIG. 16, the clamp assembly 210, to improve the securement of the bar 6 and the pin 8 within the clamp assembly 210 further includes a third spring insert 256 positioned in a spaced-apart relationship with the first spring insert 218. The third spring insert 256 is used to secure the first bar 6. The clamp assembly 210 further includes a fourth spring insert 258 spaced from the second spring insert 242. The fourth spring insert 258 is used to secure the second fixation bar 54 in fourth passage 258.

Figure 17:
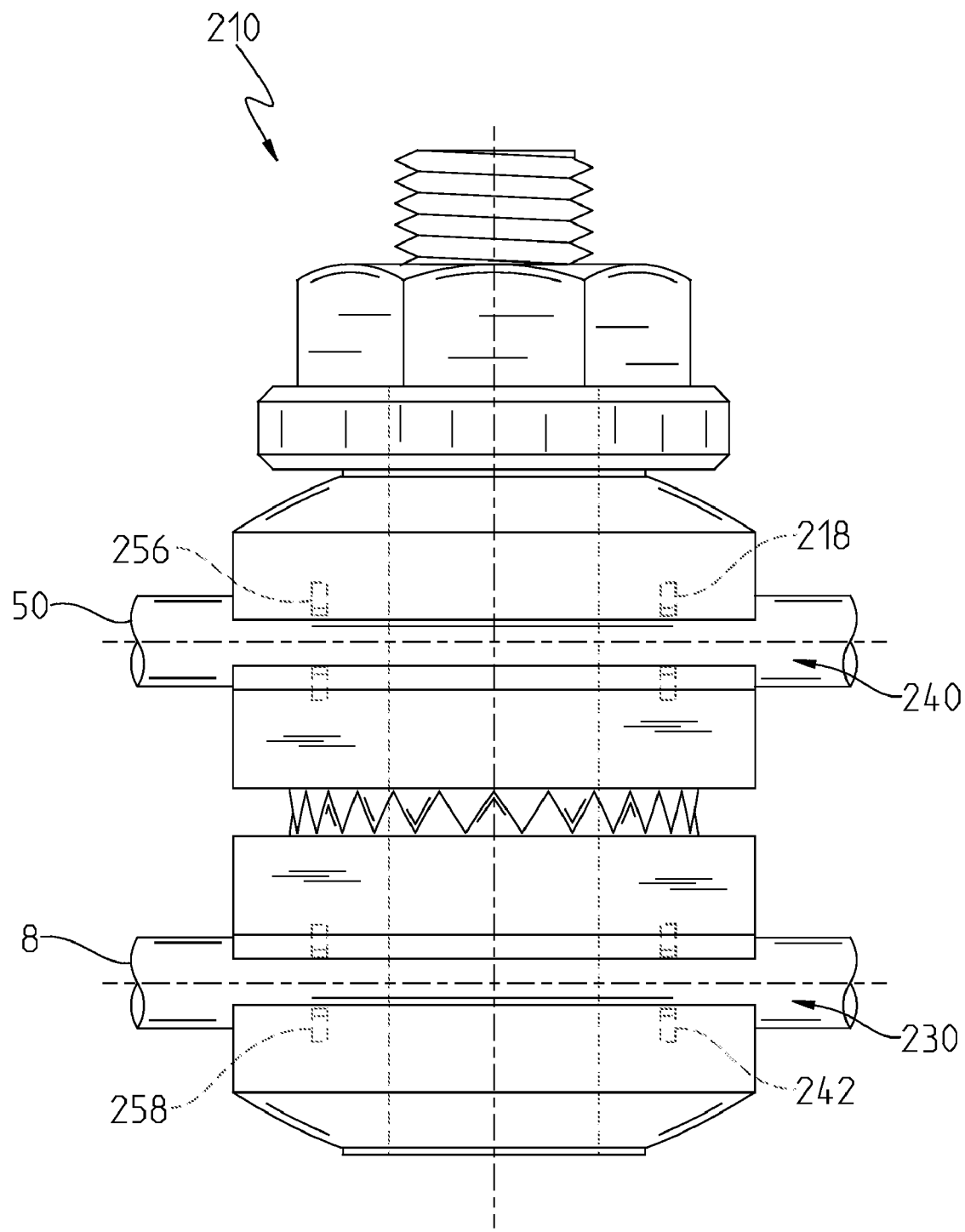
FIG. 17 depicts a side view of the clamp assembly of FIG. 13 showing the spring inserts engaging the pins.

Referring now to FIG. 17, third spring insert 256 is further used for securing second fixation pin 50 within third passage 240. Similarly, the fourth spring insert 258 is utilized further to secure the first fixation pin 8 within the second passage 230.

Referring now to FIGS. 18-23, another embodiment of the present disclosure is shown as clamp assembly 310. The clamp assembly 310 is utilized in external fixator system 302. The external fixator system 302 is similar to the external fixator system 2 of FIG. 1 except that the external fixator system 302 uses clamp assembly 310 in place of clamp assembly 10 that is used in the external fixator system 302 of FIG. 1.

The clamp assembly 310 is similar to the clamp assembly 10 of FIGS. 2-8 except that the clamp assembly 310 includes a spring insert that is different in comparison to the spring insert used in the clamp assembly 10 of FIGS. 2-8. The clamp assembly 310 utilizes a spring insert that extends into two spaced-apart passages and that has four spaced-apart fingers, with two fingers that grasp the fixation member in a spaced-apart relationship within each passage. As such, each spring insert of the external fixator system 310 replaces four of the spring inserts that are utilized in the clamp assembly 10 of FIGS. 2-8 or replaces two of the spring inserts that are utilized in the clamp assembly 210 of FIGS. 13-17.

Figure 18:
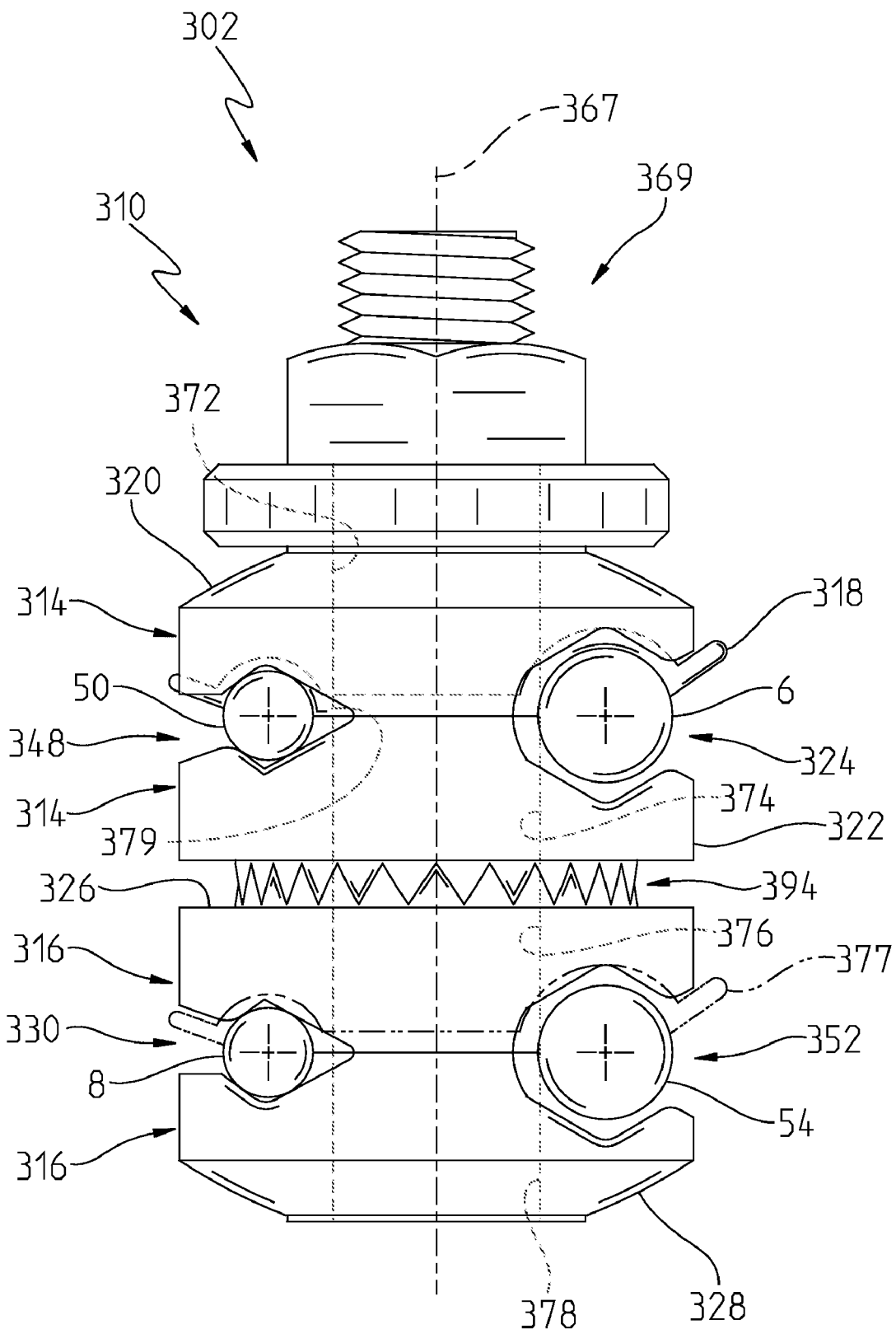
FIG. 18 depicts a plan view, partially in cross section, of another embodiment of a clamp assembly for use in the external fixator system of FIG. 1 having spring inserts with a central portion and opposed clamping ends for engaging a pin and a bar, each end having a pair of spaced apart fingers.

The clamp assembly 310, as shown in FIG. 18, includes a first jaw pair 314 and a second jaw pair 316. The second jaw pair 316 is rotatably positionable with respect to the first jaw pair 314 about center-line 367 of the clamp assembly 310. The first jaw pair 314 is connected to the second jaw pair 316 at connector 394, which is similar to connector 94 of the clamp assembly 10 of FIGS. 2-8. The first jaw pair 314 includes a first upper jaw component 320 and a first lower jaw component 322 which forms first passage 324 between the first upper jaw component 320 and the first lower jaw component 322. The jaw components 320 and 322 also define a third passage 348 between the jaw component 320 and jaw component 322.

The second jaw pair 316 includes a second upper jaw component 326 and a second lower jaw component 328 which form second passage 330 and fourth passage 352, respectively, therebetween. The passages 324, 330, 348 and 352 may be sized for any external fixator and, as shown, are sized for fixator bars or fixator pins. For example, and as shown in FIG. 18, the first passage 324 receives first fixator bar 6, the second passage 330 receives first fixation pin 8, the third passage 348 receives second pin 50 and the fourth passage 352 receives second fixation bar 54. The first fixation bar 6 is positioned in first passage 324 by first spring insert 318 that positively positions the first fixation bar 6 in the first passage 324 while the external fixator system 302 is oriented.

The first upper jaw component 320 defines a first fastener passageway 372 extending through the first upper jaw component 320. The first lower jaw component 322 defines a second fastener passageway 374 extending through the first lower jaw component 322. Similarly, the second upper jaw component 326 defines a third fastener passageway 376 extending through the second upper jaw component 326. Similarly, the second lower jaw component 328 defines a fourth fastener passageway 378 extending through the second lower jaw component 328. The first spring insert 318 defines a fifth fastener passageway 379 extending through the first spring insert 318. The clamp assembly 310 further includes a fastener 369 that extends through each of the first fastener passageway 372, the second fastener passageway 374, the third fastener passageway 376, the fourth fastener passageway 378 and the fifth fastener passageway 379.

Figure 20:
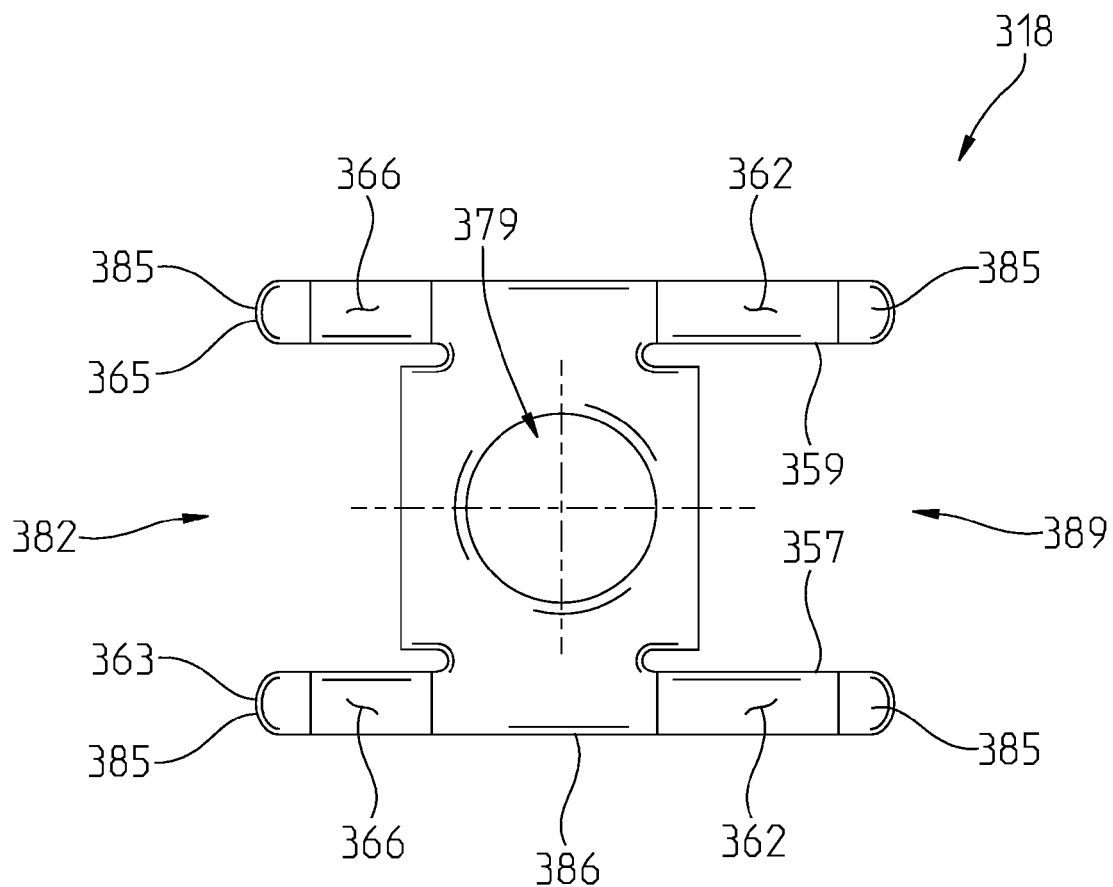
FIG. 20 depicts a top view of the spring insert of FIG. 19.
Figure 19:
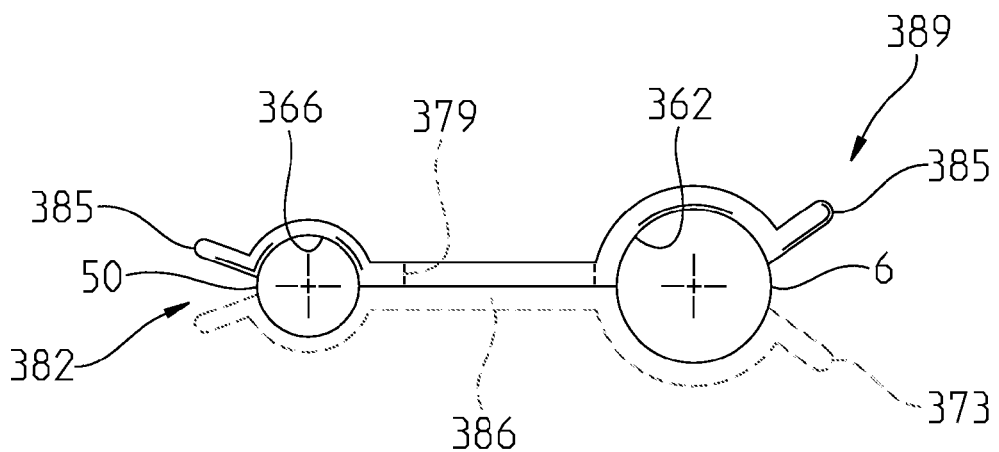
FIG. 19 depicts a plan view of the spring insert with a central portion and opposed clamping ends for engaging a pin and a bar, each end having a pair of spaced apart fingers for use in the clamp assembly of FIG. 18.

Referring now to FIGS. 19 and 20, the first spring insert 318 is shown in greater detail. The first spring insert 318, as shown in FIG. 19, includes a first engaging end 389 extending from a body 386 and a second engaging end 382 opposed to the first engaging end 389 and extending from body 386. The first engaging end 389 includes a first concave contact surface 362 for engagement with the first fixation bar 6, as well as, a nose 385 extending from the first concave contact surface 362. Similarly, the second engaging end 382 includes a third concave contact surface 366 for engagement with second pin 50. The second engaging end 382 further includes a nose 385 extending from the concave contact surface 366.

The first spring insert 318 may alternately be utilized to serve to bias both the top and the bottom of the fixating members by positioning an additional spring insert identical to first spring insert 318 in symmetrical arrangement with the first spring insert 318. For example, an additional spring insert 373, as shown in phantom, may be positioned against first spring insert 318 to provide a spring insert that engages opposed surfaces of the fixation members.

Referring now to FIG. 20, the first engaging end 389 includes a first bar finger 357 and a spaced-apart second bar finger 359. The bar fingers 357 and 359 include the concave surfaces 362 and the noses 385. The second engaging end 382 includes a first pin finger 363 and a spaced-apart second pin finger 365. The pin fingers 363 and 365 define the third concave contact surface 366 as well as the noses 385 that extend from the third concave contact surface 366. The first spring insert 318 includes the body 386 from which fifth fastener passageway 379 is formed. The fifth fastener passageway 379, in cooperation with the fastener 369, serves to orient the first spring insert 318 within the clamp assembly 310.

Figure 21:
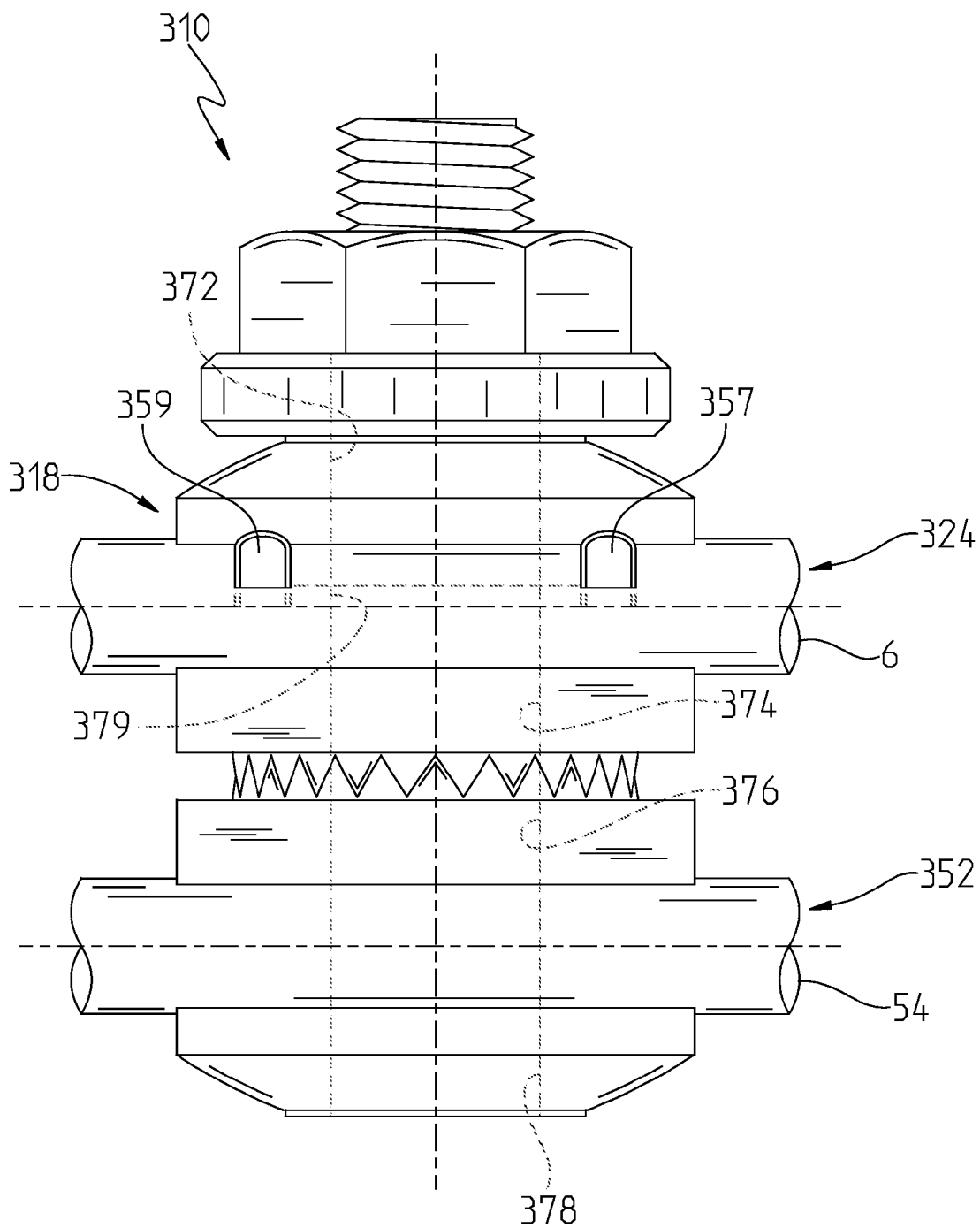
FIG. 21 depicts a side view of the clamp assembly of FIG. 19 showing the spring inserts engaging the bars.
Figure 22:
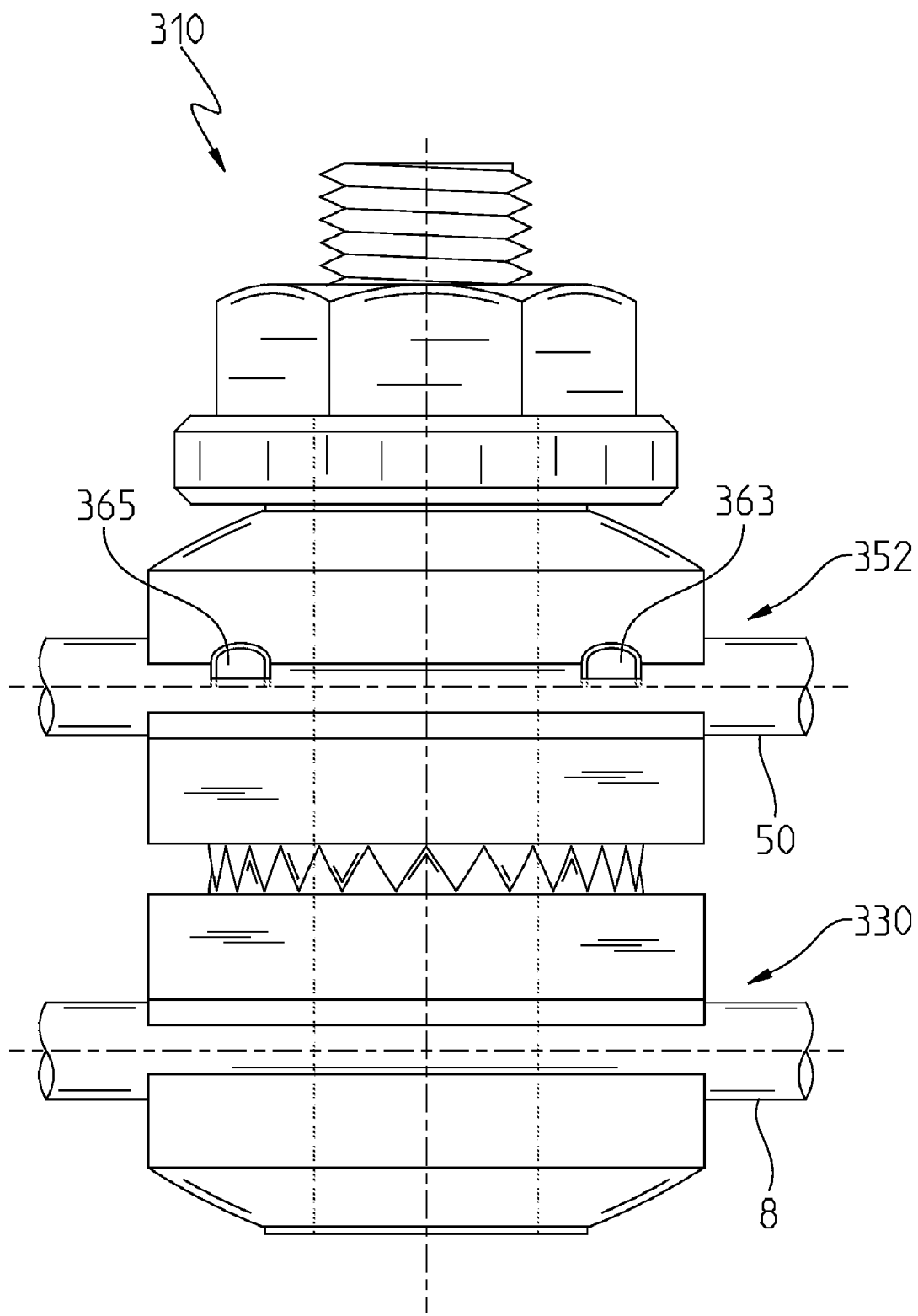
FIG. 22 depicts a side view of the clamp assembly of FIG. 19 showing the spring inserts engaging the pins.
Figure 23:
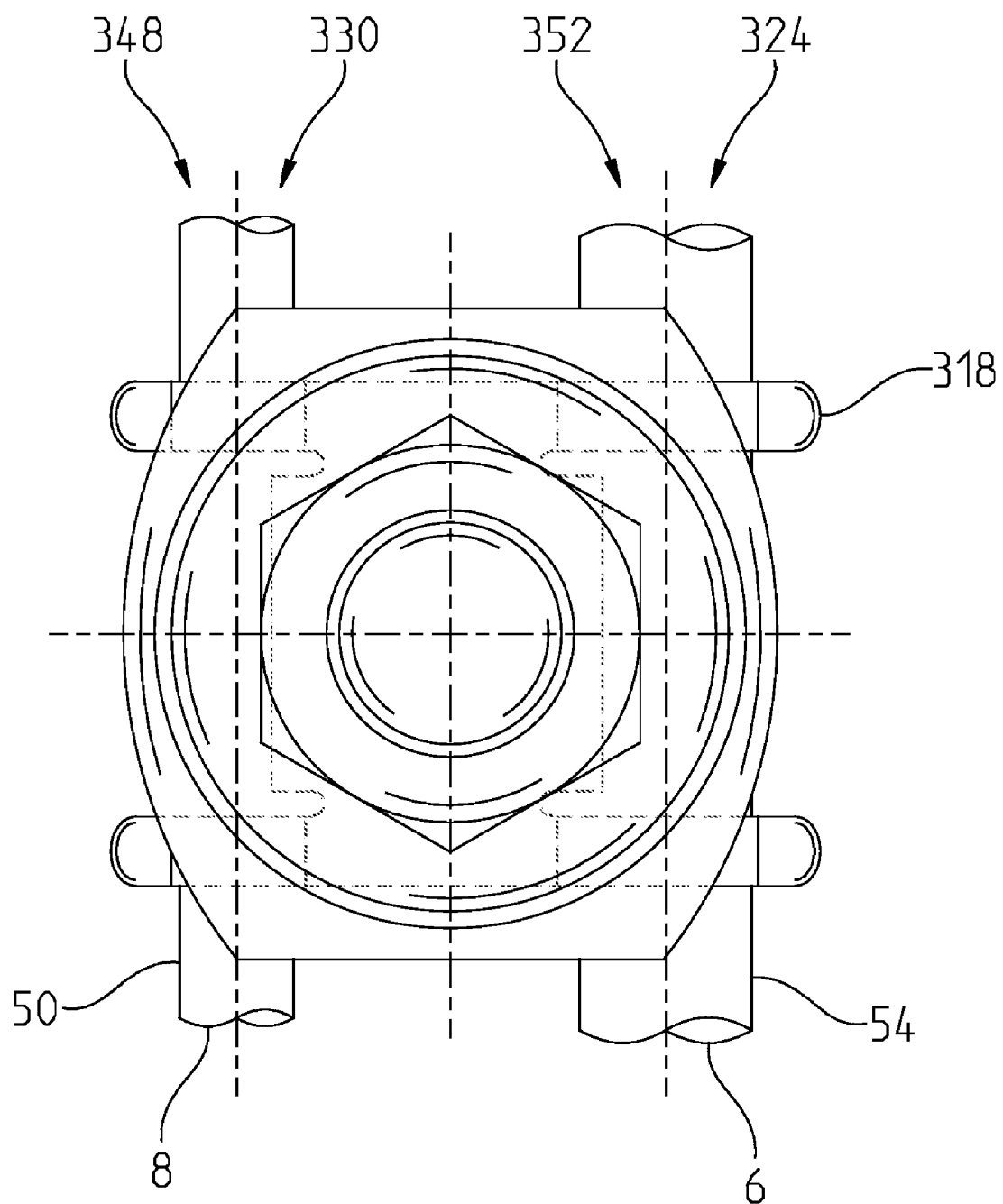
FIG. 23 depicts a top view of the clamp assembly of FIG. 19 showing the spring inserts engaging the pin and the bar.

Referring now to FIGS. 21-23, the first bar finger 357 and the second bar finger 359 extend into passage 324 and serve to position the bar 6. Similarly and referring now to FIG. 22, the first pin finger 363 and the second pin finger 365 extend into second passage 352 and are used to urge second pin 30 into a known position within the fourth passage 352.

Referring again to FIG. 18, the first spring insert 318 is shown in position in first passage 324 and in third passage 348 in solid. The first spring insert 318 may also be positioned within the second jaw pair 316, as shown in phantom as 377. The first spring insert 318, when positioned in the position 377 as shown in phantom, extends into second passage 330 and fourth passage 352. The first spring insert 318 in position in the second jaw pair 318 urges the first fixation pin 8 and the second fixation bar 54 into a positive position within the respective passages 330 and 352.

Of course, numerous other adaptations are possible. Moreover, there are advantages to individual advancements described herein that may be obtained without incorporating other aspects described above. Therefore, the spirit and scope of the appended claims should not be limited to the description of the preferred embodiments contained herein.

I claim:

1. An external fixator system, comprising:
a fixation bar;
a fixation pin; and
a clamp assembly including:
a first jaw pair having a first upper jaw component and a first lower jaw component that collectively define a first passage configured to receive said fixation bar,
a second jaw pair having a second upper jaw component and a second lower jaw component that collectively define a second passage configured to receive said fixation pin, and
a first spring insert positioned within said first passage and interposed between said first upper jaw component and said first lower jaw component,
wherein advancement of said fixation bar into said first passage causes deflection of said first spring insert.

2. The system of claim 1, wherein:
said clamp assembly further includes a second spring insert positioned within said second passage and interposed between said second upper jaw component and second lower jaw component, and
advancement of said fixation pin into said second passage causes deflection of said second spring insert.

3. The system of claim 2, wherein:
said first upper jaw component defines a first fastener passageway extending therethrough,
said first lower jaw component defines a second fastener passageway extending therethrough,
said second upper jaw component defines a third fastener passageway extending therethrough,
said second lower jaw component defines a fourth fastener passageway extending therethrough,
said clamp assembly further includes a fastener extending through each of said first fastener passageway, said second fastener passageway, said third fastener passageway, and said fourth fastener passageway.

4. The system of claim 3, wherein each of said first spring insert and said second spring insert is spaced apart from said fastener.

5. The system of claim 1, wherein:
said first upper jaw component defines a first fastener passageway extending therethrough,
said first lower jaw component defines a second fastener passageway extending therethrough,
said second upper jaw component defines a third fastener passageway extending therethrough,
said second lower jaw component defines a fourth fastener passageway extending therethrough,
said first spring insert defines a fifth fastener passageway extending therethrough, and
said clamp assembly further includes a fastener extending through each of said first fastener passageway, said second fastener passageway, said third fastener passageway, said fourth fastener passageway, and said fifth fastener passageway.

6. The system of claim 1, wherein:
said first upper jaw component and said first lower jaw component collectively define a third passage configured to receive a first additional fixation member, and
said second upper jaw component and said second lower jaw component collectively define a fourth passage configured to receive a second additional fixation member.

7. The system of claim 6, wherein:
said first spring insert is further positioned within said third passage, and
advancement of said first additional fixation member into said third passage causes deflection of said first spring insert.

8. The system of claim 6, wherein:
said first spring insert is further positioned within said third passage,
advancement of said first additional fixation member into said third passage causes deflection of said first spring insert,
said second spring insert is further positioned within said fourth passage, and advancement of said second additional fixation member into said fourth passage causes deflection of said second spring insert.

9. The system of claim 2, wherein:
said first upper jaw component and said first lower jaw component collectively define a third passage configured to receive a first additional fixation member,
said second upper jaw component and said second lower jaw component collectively define a fourth passage configured to receive a second additional fixation member,
said clamp assembly further includes a third spring insert positioned within said third passage and interposed between said first upper jaw component and said first lower jaw component, and
advancement of said first additional fixation member into said third passage causes deflection of said third spring insert.

10. The system of claim 9, wherein:
said clamp assembly further includes a fourth spring insert positioned within said fourth passage and interposed between said second upper jaw component and said second lower jaw component, and
advancement of said second additional fixation member into said fourth passage causes deflection of said fourth spring insert.

11. The system of claim 1, wherein:
said first spring insert includes a first concave contact surface, and
said first concave contact surface is positioned in contact with said fixation bar when said fixation bar is located within said first passage.

12. The system of claim 2, wherein:
said first spring insert includes a first concave contact surface,
said first concave contact surface is positioned in contact with said fixation bar when said fixation bar is located within said first passage,
said second spring insert includes a second concave contact surface, and
said second concave contact surface is positioned in contact with said fixation pin when said fixation pin is located within said second passage.

13. The system of claim 7, wherein:
said first spring insert includes a first concave contact surface and a second concave contact surface,
said first concave contact surface is positioned in contact with said fixation bar when said fixation bar is located within said first passage, and
said second concave contact surface is positioned in contact with said first additional fixation member when said first additional fixation member is located within said third passage.

14. The system of claim 8, wherein:
said first spring insert includes a first concave contact surface and a second concave contact surface,
said second spring insert includes a third concave contact surface and a fourth concave contact surface,
said first concave contact surface is positioned in contact with said fixation bar when said fixation bar is located within said first passage, and
said second concave contact surface is positioned in contact with said first additional fixation member when said first additional fixation member is located within said third passage,
said third concave contact surface is positioned in contact with said fixation pin when said fixation pin is located within said third passage, and
said fourth concave contact surface is positioned in contact with said second additional fixation member when said second additional fixation member is located within said fourth passage.

15. The system of claim 10, wherein:
said first spring insert includes a first concave contact surface,
said second spring insert includes a second concave contact surface,
said third spring insert includes a third concave contact surface,
said fourth spring insert includes a fourth concave contact surface,
said first concave contact surface is positioned in contact with said fixation bar when said fixation bar is located within said first passage, and
said second concave contact surface is positioned in contact with said fixation pin member when said fixation pin is located within said second passage,
said third concave contact surface is positioned in contact with said first additional fixation member when said first additional fixation member is located within said third passage, and
said fourth concave contact surface is positioned in contact with said second additional fixation member when said second additional fixation member is located within said fourth passage.

* * * * *

UNITED STATES PATENT AND TRADEMARK OFFICE
CERTIFICATE OF CORRECTION

PATENT NO. : 8,187,274 B2 Page 1 of 1
APPLICATION NO. : 12/165251
DATED : May 29, 2012
INVENTOR(S) : Dale R. Schulze It is certified that error appears in the above-identified patent and that said Letters Patent is hereby corrected as shown below:

In the Specifications

Column 1,
Line 44, replace "orietations" with --orientations--

Column 1,
Line 47, after "similar" insert --to--

Column 5,
Lines 26-27, replace "FIG. 2. The" with --FIG. 2, the--

Column 6,
Line 3, replace "components 22, 20, 26 and 28" with --components 20, 22, 26 and 28--

Column 8,
Line 36, replace "first jaw pair 16" with --first jaw pair 14--

Column 8,
Line 62, replace "defined" with --define--

Column 11,
Line 9, after "second spring insert 242" insert --.--

Signed and Sealed this
Fourth Day of June, 2013

Teresa Stanek Rea
*Acting Director of the United States Patent and Trademark Office*